(12) United States Patent
Chatelier et al.

(10) Patent No.: US 8,932,445 B2
(45) Date of Patent: Jan. 13, 2015

(54) SYSTEMS AND METHODS FOR IMPROVED STABILITY OF ELECTROCHEMICAL SENSORS

(75) Inventors: Ronald C. Chatelier, Bayswater (AU); Alastair M. Hodges, Blackburn South (AU)

(73) Assignee: Cilag GmbH International (CH)

( * ) Notice: Subject to any disclaimer, the term of this patent is extended or adjusted under 35 U.S.C. 154(b) by 500 days.

(21) Appl. No.: 12/895,168

(22) Filed: Sep. 30, 2010

(65) Prior Publication Data

US 2012/0080326 A1    Apr. 5, 2012

(51) Int. Cl.
| | | |
|---|---|---|
| G01N 33/487 | (2006.01) | |
| G01N 33/543 | (2006.01) | |
| C12Q 1/00 | (2006.01) | |
| C12Q 1/54 | (2006.01) | |
| G01N 27/327 | (2006.01) | |

(52) U.S. Cl.
CPC ........ *G01N 27/3274* (2013.01); *G01N 33/5438* (2013.01); *C12Q 1/001* (2013.01); *C12Q 1/54* (2013.01)
USPC .............. 204/403.01; 205/777.5; 204/403.02; 204/403.03

(58) Field of Classification Search
CPC .................................................. G01N 27/3272
USPC ............. 204/401.01–403.15; 205/777.5–778, 205/792
See application file for complete search history.

(56) References Cited

U.S. PATENT DOCUMENTS

| | | |
|---|---|---|
| 5,385,846 A | 1/1995 | Kuhn et al. |
| 5,620,579 A | 4/1997 | Genshaw et al. |
| 5,653,863 A | 8/1997 | Genshaw et al. |
| 5,781,455 A | 7/1998 | Hyodo |
| 5,858,648 A | 1/1999 | Steel et al. |
| 5,942,102 A | 8/1999 | Hodges et al. |
| 6,174,420 B1 | 1/2001 | Hodges et al. |
| 6,193,873 B1 | 2/2001 | Ohara et al. |

(Continued)

FOREIGN PATENT DOCUMENTS

| | | |
|---|---|---|
| CN | 1646900 A | 7/2005 |
| EP | 0735363 A1 | 10/1996 |

(Continued)

OTHER PUBLICATIONS

Australian Examiner's first report for Application No. 2010257395 dated Jun. 28, 2011 (2 Pages).

(Continued)

*Primary Examiner* — Bach Dinh
(74) *Attorney, Agent, or Firm* — Hiscock & Barclay, LLP

(57) ABSTRACT

Methods for determining a concentration of an analyte in a sample, and the devices and systems used in conjunction with the same, are provided herein. In one exemplary embodiment of a method for determining a concentration of an analyte in a sample, a sample including an analyte is provided in a sample analyzing device having a working and a counter electrode. An electric potential is applied between the electrodes and a measurement of a parameter correlating to changes in a physical property of the sample analyzing device is calculated. A concentration of the analyte in view of the parameter correlating to a change in the physical property can then be determined Systems and devices that take advantage of the parameter correlating to changes in a physical property to make analyte concentration determinations are also provided.

20 Claims, 8 Drawing Sheets

(56) References Cited

U.S. PATENT DOCUMENTS

| | | |
|---|---|---|
| 6,241,862 B1 | 6/2001 | McAleer et al. |
| 6,284,125 B1 | 9/2001 | Hodges et al. |
| 6,379,513 B1 | 4/2002 | Chambers et al. |
| 6,413,410 B1 | 7/2002 | Hodges et al. |
| 6,424,847 B1 | 7/2002 | Mastrototaro et al. |
| 6,475,360 B1 | 11/2002 | Hodges et al. |
| 6,475,372 B1 | 11/2002 | Ohara et al. |
| 6,521,110 B1 | 2/2003 | Hodges et al. |
| 6,576,117 B1 | 6/2003 | Iketaki et al. |
| 6,599,407 B2 | 7/2003 | Taniike et al. |
| 6,632,349 B1 | 10/2003 | Hodges et al. |
| 6,638,415 B1 | 10/2003 | Hodges et al. |
| 6,676,995 B2 | 1/2004 | Dick et al. |
| 6,749,887 B1 | 6/2004 | Dick et al. |
| 6,780,645 B2 | 8/2004 | Hayter et al. |
| 6,797,150 B2 | 9/2004 | Kermani et al. |
| 6,830,934 B1 | 12/2004 | Harding et al. |
| 6,856,125 B2 | 2/2005 | Kermani |
| 6,869,411 B2 | 3/2005 | Langley et al. |
| 6,872,298 B2 | 3/2005 | Kermani |
| 6,895,263 B2 | 5/2005 | Shin et al. |
| 6,946,067 B2 | 9/2005 | Hodges et al. |
| 7,043,821 B2 | 5/2006 | Hodges |
| 7,045,054 B1 | 5/2006 | Buck et al. |
| 7,195,704 B2 | 3/2007 | Kermani et al. |
| 7,199,594 B2 | 4/2007 | Kermani |
| 7,288,174 B2 | 10/2007 | Cui et al. |
| 7,291,256 B2 | 11/2007 | Teodorczyk et al. |
| 7,338,639 B2 | 3/2008 | Burke et al. |
| 7,390,667 B2 | 6/2008 | Burke et al. |
| 7,407,811 B2 | 8/2008 | Burke et al. |
| 7,431,820 B2 | 10/2008 | Hodges |
| 7,452,457 B2 | 11/2008 | Burke et al. |
| 7,488,601 B2 | 2/2009 | Burke et al. |
| 7,597,793 B2 | 10/2009 | Burke et al. |
| 7,749,371 B2 | 7/2010 | Guo et al. |
| 7,771,583 B2 | 8/2010 | Diamond et al. |
| 7,923,258 B2 | 4/2011 | Heller |
| 8,101,065 B2 | 1/2012 | Chatelier et al. |
| 2002/0150896 A1 | 10/2002 | Polonsky et al. |
| 2003/0094383 A1* | 5/2003 | Kermani ............... 205/777.5 |
| 2003/0155237 A1 | 8/2003 | Surridge et al. |
| 2003/0180814 A1 | 9/2003 | Hodges et al. |
| 2003/0201194 A1 | 10/2003 | Heller et al. |
| 2003/0203498 A1 | 10/2003 | Neel et al. |
| 2004/0079652 A1 | 4/2004 | Vreeke et al. |
| 2004/0120848 A1 | 6/2004 | Teodorczyk |
| 2004/0182703 A1 | 9/2004 | Bell et al. |
| 2004/0203137 A1 | 10/2004 | Hodges et al. |
| 2004/0256248 A1 | 12/2004 | Burke et al. |
| 2005/0004439 A1 | 1/2005 | Shin et al. |
| 2005/0023154 A1* | 2/2005 | Kermani et al. ............. 205/775 |
| 2005/0161344 A1* | 7/2005 | Kermani et al. ........... 205/777.5 |
| 2006/0108236 A1 | 5/2006 | Kasielke et al. |
| 2006/0134713 A1 | 6/2006 | Rylatt et al. |
| 2006/0200017 A1 | 9/2006 | Monfre et al. |
| 2006/0217602 A1 | 9/2006 | Abul-Haj et al. |
| 2007/0017824 A1* | 1/2007 | Rippeth et al. ................ 205/792 |
| 2007/0024287 A1 | 2/2007 | Graves et al. |
| 2007/0034529 A1 | 2/2007 | Bard et al. |
| 2007/0074977 A1* | 4/2007 | Guo et al. .................... 205/792 |
| 2007/0131565 A1 | 6/2007 | Fujiwara et al. |
| 2007/0154951 A1 | 7/2007 | Kermani |
| 2007/0227912 A1 | 10/2007 | Chatelier et al. |
| 2007/0231914 A1 | 10/2007 | Deng et al. |
| 2007/0235346 A1 | 10/2007 | Popovich et al. |
| 2007/0235347 A1* | 10/2007 | Chatelier et al. .............. 205/792 |
| 2008/0093230 A1 | 4/2008 | Diamond et al. |
| 2008/0098802 A1 | 5/2008 | Burke et al. |
| 2008/0105568 A1 | 5/2008 | Wu |
| 2008/0173552 A1 | 7/2008 | Wu et al. |
| 2008/0179197 A1 | 7/2008 | Wu |
| 2008/0199894 A1 | 8/2008 | Galasso |
| 2008/0214910 A1 | 9/2008 | Buck |
| 2008/0274447 A1 | 11/2008 | Mecklenburg |
| 2008/0293082 A1 | 11/2008 | Heller |
| 2009/0000959 A1 | 1/2009 | Feldman et al. |
| 2009/0005666 A1 | 1/2009 | Shin et al. |
| 2009/0017483 A1 | 1/2009 | Yamaoka et al. |
| 2009/0042306 A1 | 2/2009 | Reynolds et al. |
| 2009/0045076 A1 | 2/2009 | Burke et al. |
| 2009/0084687 A1 | 4/2009 | Chatelier et al. |
| 2009/0089010 A1 | 4/2009 | Burke et al. |
| 2009/0101523 A1 | 4/2009 | Deng |
| 2009/0112478 A1 | 4/2009 | Mueller, Jr. et al. |
| 2009/0157344 A1 | 6/2009 | Burke et al. |
| 2009/0184004 A1* | 7/2009 | Chatelier et al. ........... 205/777.5 |
| 2009/0292489 A1 | 11/2009 | Burke et al. |
| 2009/0301899 A1 | 12/2009 | Hodges et al. |
| 2010/0006452 A1 | 1/2010 | Hodges et al. |
| 2010/0089775 A1 | 4/2010 | Chen et al. |
| 2010/0173396 A1 | 7/2010 | Miller et al. |
| 2010/0270178 A1 | 10/2010 | Guo et al. |
| 2011/0073493 A1 | 3/2011 | Chatelier et al. |
| 2011/0155584 A1 | 6/2011 | Chatelier et al. |
| 2011/0155585 A1 | 6/2011 | Chatelier et al. |
| 2011/0155589 A1 | 6/2011 | Chatelier et al. |

FOREIGN PATENT DOCUMENTS

| | | |
|---|---|---|
| EP | 1 312 919 A2 | 5/2003 |
| EP | 1 729 119 A1 | 12/2006 |
| EP | 1839571 A1 | 10/2007 |
| WO | 03/069304 A2 | 8/2003 |
| WO | WO 03/069304 A2 | 8/2003 |
| WO | 2006/036833 A2 | 4/2006 |
| WO | WO-2008150436 A1 | 12/2008 |
| WO | 2009/140343 A1 | 11/2009 |

OTHER PUBLICATIONS

Australian Notice of Acceptance issued Oct. 27, 2011 for Application No. 2010257465 (3 Pages).

International Search Report and Written Opinion in PCT/IB2011/002472, dated Dec. 29, 2011 (12 Pages).

International Search Report and Written Opinion in PCT/US10/62629, dated Feb. 23, 2011.

Extended EP Search Report in EP 10252245.5, dated Jul. 7, 2011.

"WaveSense White Paper: Performance of the WaveSense KeyNote Blood Glucose Monitoring System Across 23 Lots of Test Strips", WaveSense, Mar. 2007, XP002640744, URL: http://www.wavesense.info/uploads/pdf/23lotstudyKeyNote.pdf.pdf.

AU Patent Examination Report for 2011309771; dated Sep. 19, 2013, 3 pgs.

EP Search Report for 13 166 558.0; dated Sep. 10, 2013; 6 pgs.

Chinese Office Action and Search Report for CN 201180057833.6; dated Jul. 2, 2014; 16 pages.

* cited by examiner

SYSTEMS AND METHODS FOR IMPROVED STABILITY OF ELECTROCHEMICAL SENSORS

FIELD

The system and method provided herein relates to the field of medical testing, in particular the detection of the presence and/or concentration of an analyte(s) within a sample (e.g., physiological fluids including blood).

BACKGROUND

Analyte concentration determination in physiological fluids (e.g., blood or blood derived products such as plasma) is of ever increasing importance in today's society. Such assays find use in a variety of applications and settings, including clinical laboratory testing, home testing, etc., where the results of such testing play a prominent role in the diagnosis and management of a variety of disease conditions. Analytes of interest include glucose for diabetes management, cholesterol for monitoring cardiovascular conditions, and the like.

A common method for analyte concentration determination assays is based on electrochemistry. In such methods, an aqueous liquid sample is placed into a sample reaction chamber in a sensor, e.g., an electrochemical cell made up of at least two electrodes, i.e., a working electrode and a counter electrode, where the electrodes have an impedance that renders them suitable for amperometric or coulometric measurement. The component to be analyzed is allowed to react with a reagent to form an oxidizable (or reducible) substance in an amount proportional to the analyte concentration. The quantity of the oxidizable (or reducible) substance present is then estimated electrochemically and related to the analyte concentration in the sample.

A desirable attribute of all sensor elements is that they have a long shelf life—that is, the sensing characteristic of the sensor element does not change significantly between manufacture and use (i.e. during storage). However, when stored for long periods of time and/or in non-optimal storage conditions, e.g., high temperatures, high humidity, etc., the performance of sensors can degrade. For example, the accuracy of analyte concentration determinations made using such sensors can be reduced. It is an object of the present invention to overcome or ameliorate these and other disadvantages in the prior art.

SUMMARY

Various aspects of a system and method for determining a concentration of an analyte in a sample are provided herein. In one such aspect, the systems and methods include using an electrochemical cell in which a potential is applied and a current is measured. A parameter correlating to a physical property of the electrochemical cell can also be measured. Based on the current measurements and the parameter correlating to a physical property, the methods and systems allow analyte concentration to be found in a rapid manner while minimizing the effect of the physical property of the electrochemical cell.

In the various embodiments discussed below, the electrochemical cell can be in used in various sample analyzing devices such as glucose sensors or immunosensors. The analyzed sample can include blood. In one embodiment the blood can include whole blood. The analyte for which the concentration is being analyzed can include glucose. The assaying of a glucose concentration may include an oxidation of glucose into gluconic acid. In an embodiment, the enzyme GDH with the flavin adenine dinucleotide (FAD) co-factor may be used to catalyze the transformation of glucose into gluconic acid. In embodiments in which the sample analyzing device is an immunosensor, the analyte for which the concentration is being analyzed can include C-reactive protein.

In one aspect, a method for determining a concentration of an analyte in a sample is disclosed. The method includes introducing a sample into an electrochemical cell of a sample analyzing device to cause a transformation of the analyte. A variety of electrochemical cells can be used, including for example a cell having first and second electrodes in a spaced apart relationship and a reagent. Once the sample is introduced, the method includes determining a measurement of a parameter correlating to a physical property of the electrochemical cell and calculating a correction factor where the correction factor is in view of at least the parameter correlating to the physical property of the electrochemical cell. The method then includes determining a concentration of the analyte in view of the correction factor.

In another aspect, an electrochemical system is disclosed. The electrochemical system can include an electrochemical cell having a first electrode and a second electrode, and a meter connected to the electrochemical cell. The meter can include a control unit connected to the electrochemical cell so that the control unit applies a potential between the first electrode and the second electrode of the electrochemical cell and the control unit determines a measurement of a parameter correlating to a physical property of the electrochemical cell and uses said measurement to calculate a corrected concentration of an analyte in the sample In some embodiments, the physical property to which the correction factor correlates can be related to at least one of an age of the electrochemical cell and a storage condition of the electrochemical cell. For example, the storage condition can include a storage temperature and a storage time. In one aspect, the parameter correlating to a physical property of the electrochemical cell can include a measured capacitance of the electrochemical cell.

In another aspect, a method for measuring a corrected analyte concentration is provided. The method includes applying a sample to a test strip. Once the sample is applied, the method includes applying a first test voltage for a first time interval between a first electrode and a second electrode sufficient to oxidize a reduced mediator at the second electrode. Following the application of the first test voltage, the method includes applying a second test voltage for a second time interval between the first electrode and the second electrode sufficient to oxidize the reduced mediator at the first electrode. A first glucose concentration can then be calculated based on test current values during the first time interval and the second time interval.

The method can also include determining a capacitance of the test strip and calculating a capacitance corrected glucose concentration based on the first glucose concentration and the capacitance. For example, the step of calculating the capacitance corrected glucose concentration can include calculating a correction factor based on the capacitance and the first glucose concentration, wherein the capacitance corrected glucose concentration is calculated based on the first glucose concentration and the correction factor. For example, the correction factor can be about zero when the capacitance is about equal to a predetermined ideal capacitance of the test strip. In some embodiments, the step of calculating the capacitance corrected glucose concentration further can include dividing the correction factor by one hundred and adding one to give an intermediate term and multiplying the intermediate term by the first glucose concentration to give a capacitance corrected glucose concentration.

In some embodiments, the capacitance corrected glucose concentration can be calculated when the capacitance is less than a first capacitance threshold and the first glucose concentration is greater than a first glucose concentration threshold. In some embodiments, the method can also include determining if the correction factor is greater than a correction factor threshold value, then setting the correction factor to the correction factor threshold value.

In another aspect, an electrochemical system is disclosed. The electrochemical system can include a test strip and a test meter. The test strip can include an electrochemical cell and electrical contacts for mating with the test meter. The electrochemical cell can include a first electrode and a second electrode in a spaced apart relationship, and a reagent. The test meter can include a processor adapted to receive current data from the test strip and further adapted to determine a capacitance corrected glucose concentration based on a calculated glucose concentration and a measured capacitance. For example, the measured capacitance can correlate with a physical property of the test strip relating to at least one of an age of the test strip and a storage condition of the test strip. The storage condition can, for example, include a storage temperature and a storage time.

In one exemplary embodiment, the test meter can include data storage containing a glucose concentration threshold and a capacitance threshold. In some embodiments, for example, the processor can determine the capacitance corrected glucose concentration value when the measured capacitance is less than the capacitance threshold and the calculated glucose concentration is greater than the glucose concentration threshold.

In the various systems and methods discussed above, an exemplary method of determining a capacitance of the electrochemical cell can include applying a first test voltage between the first electrode and the second electrode. The first test voltage can have an AC voltage component and a DC voltage component and the AC voltage component can be applied at a predetermined amount of time after the application of the first test voltage. The test voltage can also have a DC voltage component that has a magnitude sufficient to cause a limiting test current at the second electrode, the second electrode not having a reagent layer coating. The method can also include processing a portion of the test currents resulting from the AC voltage component into a capacitance value of the electrochemical cell.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

Various features of the present disclosure are set forth with particularity in the appended claims. A better understanding of such features can be obtained by reference to the following detailed description that sets forth illustrative, non-limiting embodiments and the accompanying drawings of which:

DETAILED DESCRIPTION

Figures 1A, 1B, 1C:
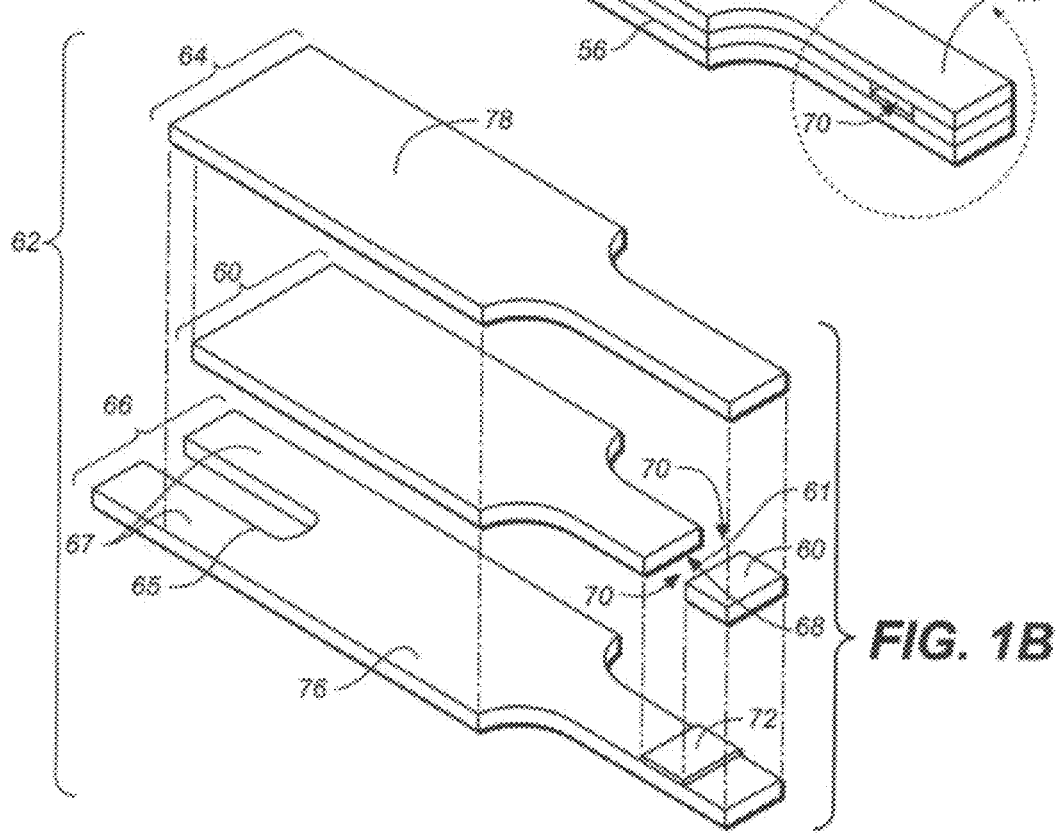
FIG. 1A illustrates a perspective view of an exemplary test strip.
FIG. 1B illustrates an exploded perspective view of the test strip of FIG. 1A.
FIG. 1C illustrates a perspective view of a distal portion of the test strip of FIG. 1A.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

The presently disclosed systems and methods are suitable for use in the determination of a wide variety of analytes in a wide variety of samples, and are particularly suited for use in the determination of analytes in whole blood, plasma, serum, interstitial fluid, or derivatives thereof. In an exemplary embodiment, a glucose test system based on a thin-layer cell design with opposing electrodes and tri-pulse electrochemical detection that is fast (e.g., about 5 second analysis time), requires a small sample (e.g., about 0.4 µL), and can provide improved reliability and accuracy of blood glucose measurements. In the reaction cell to assay analyte, glucose in the sample can be oxidized to gluconolactone using glucose dehydrogenase and an electrochemically active mediator can be used to shuttle electrons from the enzyme to a palladium working electrode. More particularly, a reagent layer coating at least one of the electrodes in the reaction cell can include glucose dehydrogenase (GDH) based on pyrroloquinoline quinone (PQQ) co-factor and ferricyanide. In another embodiment, the enzyme GDH based on the PQQ co-factor may be replaced with the enzyme GDH based on the flavin adenine dinucleotide (FAD) co-factor. When blood or control solution is dosed into the reaction chamber, glucose is oxidized by GDH(ox) and in the process converts GDH(ox) to GDH(red), as shown in the chemical transformation T.1 below. Note that GDH(ox) refers to the oxidized state of GDH, and GDH (red) refers to the reduced state of GDH.

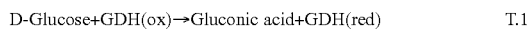

D-Glucose+GDH(ox)→Gluconic acid+GDH(red)　　　T.1

A potentiostat can be utilized to apply a tri-pulse potential waveform to the working and counter electrodes, resulting in test current transients used to calculate the glucose concentration. Further, additional information gained from the test current transients may be used to discriminate between sample matrices and correct for variability in blood samples due to hematocrit, temperature variation, electrochemically active components, and identify possible system errors.

The subject methods can be used, in principle, with any type of electrochemical cell having spaced apart first and second electrodes and a reagent layer. For example, an electrochemical cell can be in the form of a test strip. In one aspect, the test strip may include two opposing electrodes separated by a thin spacer for defining a sample-receiving chamber or zone in which a reagent layer is located. Applicants note that other types of test strips, including, for example, test strips with co-planar electrodes may also be used with the methods described herein.

Electrochemical Cells

FIGS. 1A-4B show various views of an exemplary test strip 62 suitable for use with the methods described herein. As shown, the test strip 62 can include an elongate body extending from a proximal end 80 to a distal end 82, and having lateral edges 56, 58. The proximal portion of the body 59 can include a sample reaction chamber 61 having multiple electrodes 164, 166 and a reagent 72, while the distal portion of the test strip body 59 can include features configured for electrically communicating with a test meter. In use, physiological fluid or a control solution can be delivered to the sample reaction chamber 61 for electrochemical analysis.

In the illustrative embodiment, the test strip 62 can include a first electrode layer 66 and a second electrode layer 64, with a spacer layer 60 positioned therebetween. The first electrode layer 66 can provide a first electrode 166 and a first connection track 76 for electrically connecting the first electrode 166 to a first electrical contact 67. Similarly, the second electrode layer 64 can provide a second electrode 164 and a second connection track 78 for electrically connecting the second electrode 164 with a second electrical contact 63.

In one embodiment, the sample reaction chamber 61 is defined by the first electrode 166, the second electrode 164, and a spacer 60 as shown in FIGS. 1A-4B. Specifically, the first electrode 166 and the second electrode 164 define, respectively, the bottom and top of the sample reaction chamber 61. A cutout area 68 of the spacer 60 can define the side walls of the sample reaction chamber 61. In one aspect, the sample reaction chamber 61 can further include a number of ports 70 that provide a sample inlet and/or a vent. For example, one of the ports can provide a fluid sample ingress and the other port can act as a vent.

The sample reaction chamber 61 can have a small volume. For example, the volume can range from about 0.1 microliters to about 5 microliters, preferably about 0.2 microliters to about 3 microliters, and more preferably about 0.3 microliters to about 1 microliter. As will be appreciated by those skilled in the art, the sample reaction chamber 61 can have various other such volumes. To provide the small sample volume, the cutout 68 can have an area ranging from about 0.01 cm² to about 0.2 cm², preferably about 0.02 cm² to about 0.15 cm², and more preferably about 0.03 cm² to about 0.08 cm². Similarly, those skilled in the art will appreciate that the volume cutout 68 can be of various other such areas. In addition, the first and second electrode 166, 164 can be spaced in the range of about 1 micron to about 500 microns, preferably in the range of about 10 microns to about 400 microns, and more preferably in the range of about 40 microns to about 200 microns. In other embodiments, such a range can vary between various other values. The close spacing of the electrodes can also allow redox cycling to occur, where oxidized mediator generated at the first electrode 166, can diffuse to the second electrode 164 to become reduced, and subsequently diffuse back to the first electrode 166 to become oxidized again.

Figures 2, 3, 4A:
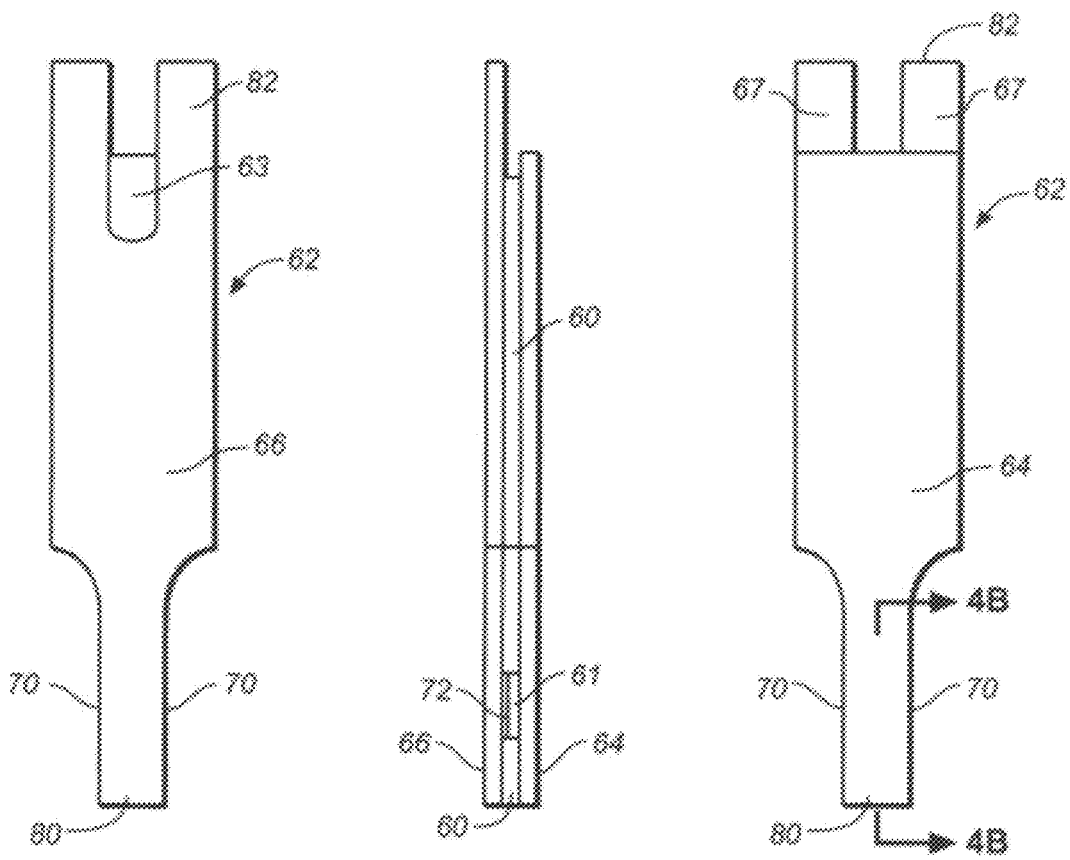
FIG. 2 illustrates a bottom plan view of the test strip of FIG. 1A.
FIG. 3 illustrates a side plan view of the test strip of FIG. 1A.
FIG. 4A illustrates a top plan view of the test strip of FIG. 1A.

At the distal end of the test strip body 59, a first electrical contact 67 can be used to establish an electrical connection to a test meter. A second electrical contact 63 can be accessed by the test meter through a U-shaped notch 65 as illustrated in FIG. 2. Applicants note that the test strip 62 can include a variety of alternative electrical contacts configured for electrically connecting to a test meter. For example, U.S. Pat. No. 6,379,513, the entirety of which is hereby incorporated herein by reference, discloses an electrochemical cell connection means.

In one embodiment, the first electrode layer 66 and/or the second electrode layer 64 can be a conductive material formed from materials such as gold, palladium, carbon, silver, platinum, tin oxide, iridium, indium, and combinations thereof (e.g., indium doped tin oxide). In addition, the electrodes can be formed by disposing a conductive material onto an insulating sheet (not shown) by various processes such as, for example, a sputtering, electroless plating, or a screen printing process. In one exemplary embodiment, the second electrode layer 64 can be a sputtered gold electrode and the first electrode layer 66 can be a sputtered palladium electrode. Suitable materials that can be employed as the spacing layer 60 include various insulating materials, such as, for example, plastics (e.g., PET, PETG, polyimide, polycarbonate, polystyrene), silicon, ceramic, glass, adhesives, and combinations thereof.

A reagent layer 72 can be disposed within the sample reaction chamber 61 using a process such as slot coating, dispensing from the end of a tube, ink jetting, and screen printing. Such processes are described, for example, in the following U.S. Pat. Nos.: 6,749,887; 6,869,411; 6,676,995; and 6,830,934, the entirety of each of these references being incorporated herein by reference. In one embodiment, the reagent layer 72 can include at least a mediator and an enzyme, and can be deposited onto the first electrode 166. Various mediators and/or enzymes are within the spirit and scope of the present disclosure. For example, suitable mediators include ferricyanide, ferrocene, ferrocene derivatives, osmium bipyridyl complexes, and quinone derivatives. Examples of suitable enzymes include glucose oxidase, glucose dehydrogenase (GDH) based on pyrroloquinoline quinone (PQQ) co-factor, GDH based on nicotinamide adenine dinucleotide co-factor, and FAD-based GDH [E.C.1.1.99.10]. One exemplary reagent formulation, which would be suitable for making the reagent layer 72, is described in pending U.S. application Ser. No. 10/242,951, entitled, "Method of Manufacturing a Sterilized and Calibrated Biosensor-Based Medical Device", published as U.S. Published Patent Application No. 2004/0120848, the entirety of which is hereby incorporated herein by reference.

Either the first electrode 166 or the second electrode 164 can function as working electrode which oxidizes or reduces a limiting amount of mediator depending on the polarity of the applied test potential of the test meter. For example, if the current limiting species is a reduced mediator, it can be oxidized at the first electrode 166 as long as a sufficiently positive potential was applied with respect to the second electrode 164. In such a situation, the first electrode 166 performs the function of the working electrode and second electrode 164 performs the function of a counter/reference electrode. It should be noted that unless otherwise stated for test strip 62, all potentials applied by test meter 100 will hereinafter be stated with respect to second electrode 164.

Similarly, if a sufficiently negative potential is applied with respect to the second electrode 164, then the reduced mediator can be oxidized at the second electrode 164. In such a situation, the second electrode 164 can perform the function of the working electrode and the first electrode 166 can perform the function of the counter/reference electrode.

Initially, the presently disclosed method can include introducing a quantity of the fluid sample of interest into the test strip 62, which includes the first electrode 166, the second electrode 164 and a reagent layer 72. The fluid sample can be whole blood or a derivative or fraction thereof, or a control solution. The fluid sample, e.g., blood, can be dosed into the sample reaction chamber 61 via the port 70. In one aspect, the port 70 and/or the sample reaction chamber 61 can be configured such that capillary action causes the fluid sample to fill the sample reaction chamber 61.

Figure 5:
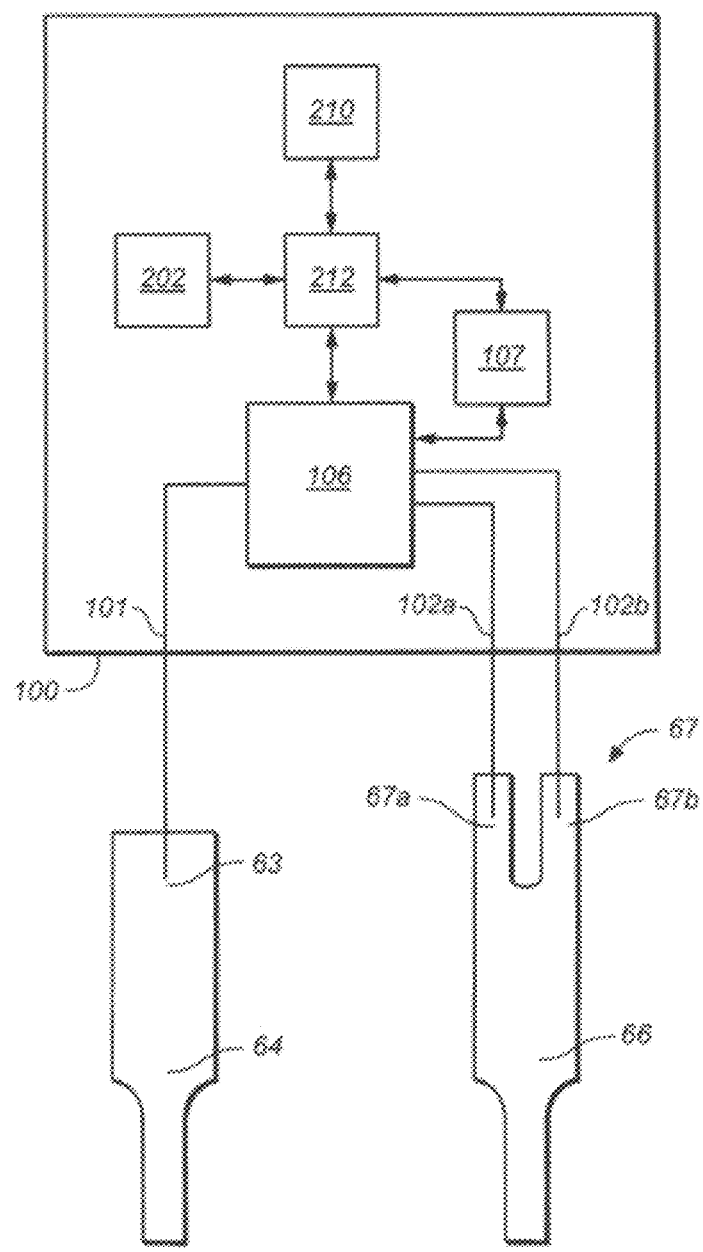
FIG. 5 illustrates a simplified schematic showing a test meter electrically interfacing with the test strip contact pads.

FIG. 5 provides a simplified schematic of a test meter 100 interfacing with a first electrical contact 67 and a second electrical contact 63, which are in electrical communication with the first electrode 166 and the second electrode 164, respectively, of the test strip 62. The test meter 100 can be configured to electrically connect to the first electrode 166 and the second electrode 164 via a first electrical contact 67 and a second electrical contact 63, respectively (as shown in FIGS. 2 and 5). As will be appreciated by those skilled in the art, a variety of test meters can be used with the method described herein. However, in one embodiment, the test meter includes at least a processor, which may include one or more control units configured for performing calculations capable of calculating a correction factor in view of at least one measured parameter correlating to a physical property of the electrochemical cell, as well as configured for data sorting and/or storage. The microprocessor can be in the form of a mixed signal microprocessor (MSP) such as, for example, the Texas Instrument MSP 430. The TI-MSP 430 can be configured to also perform a portion of the potentiostat function and the current measurement function. In addition, the MSP 430 can also include volatile and non-volatile memory. In another embodiment, many of the electronic components can be integrated with the microcontroller in the form of an application specific integrated circuit.

As illustrated in FIG. 5, an electrical contact 67 can include two prongs 67a, 67b. In one exemplary embodiment, the test meter 100 separately connects to the prongs 67a, 67b, such that when the test meter 100 interfaces with a test strip 62 a circuit is completed. The test meter 100 can measure the resistance or electrical continuity between the prongs 67a, 67b to determine whether the test strip 62 is electrically connected to the test meter 100. Applicants note that the test meter 100 can use a variety of sensors and circuits to determine when the test strip 62 is properly positioned with respect to the test meter 100.

In one embodiment, a circuit disposed in the test meter 100 can apply a test potential and/or a current between first electrical contact 67 and second electrical contact 63. Once test meter 100 recognizes that strip 62 has been inserted, test meter 100 turns on and initiates a fluid detection mode. In one embodiment, the fluid detection mode causes test meter 100 to apply a constant current of 1 microampere between first electrode 166 and second electrode 164. Because test strip 62 is initially dry, test meter 100 measures a maximum voltage, which is limited by the hardware within test meter 100. However, once a user doses a fluid sample onto inlet 70, this causes sample reaction chamber 61 to become filled. When the fluid sample bridges the gap between first electrode 166 and second electrode 164, test meter 100 will measure a decrease in measured voltage (e.g., as described in U.S. Pat. No. 6,193,873, the entirety of which being incorporated herein by reference), which is below a predetermined threshold causing test meter 100 to automatically initiate the glucose test.

It should be noted that the measured voltage may decrease below a pre-determined threshold when only a fraction of the sample reaction chamber 61 has been filled. A method of automatically recognizing that a fluid was applied does not necessarily indicate that the sample reaction chamber 61 has been completely filled, but can only confirm a presence of some amount of fluid in the sample reaction chamber 61. Once the test meter 100 determines that a fluid has been applied to test strip 62, a short, but non-zero amount of time may still be required to allow the fluid to completely fill the sample reaction chamber 61.

Figure 6:
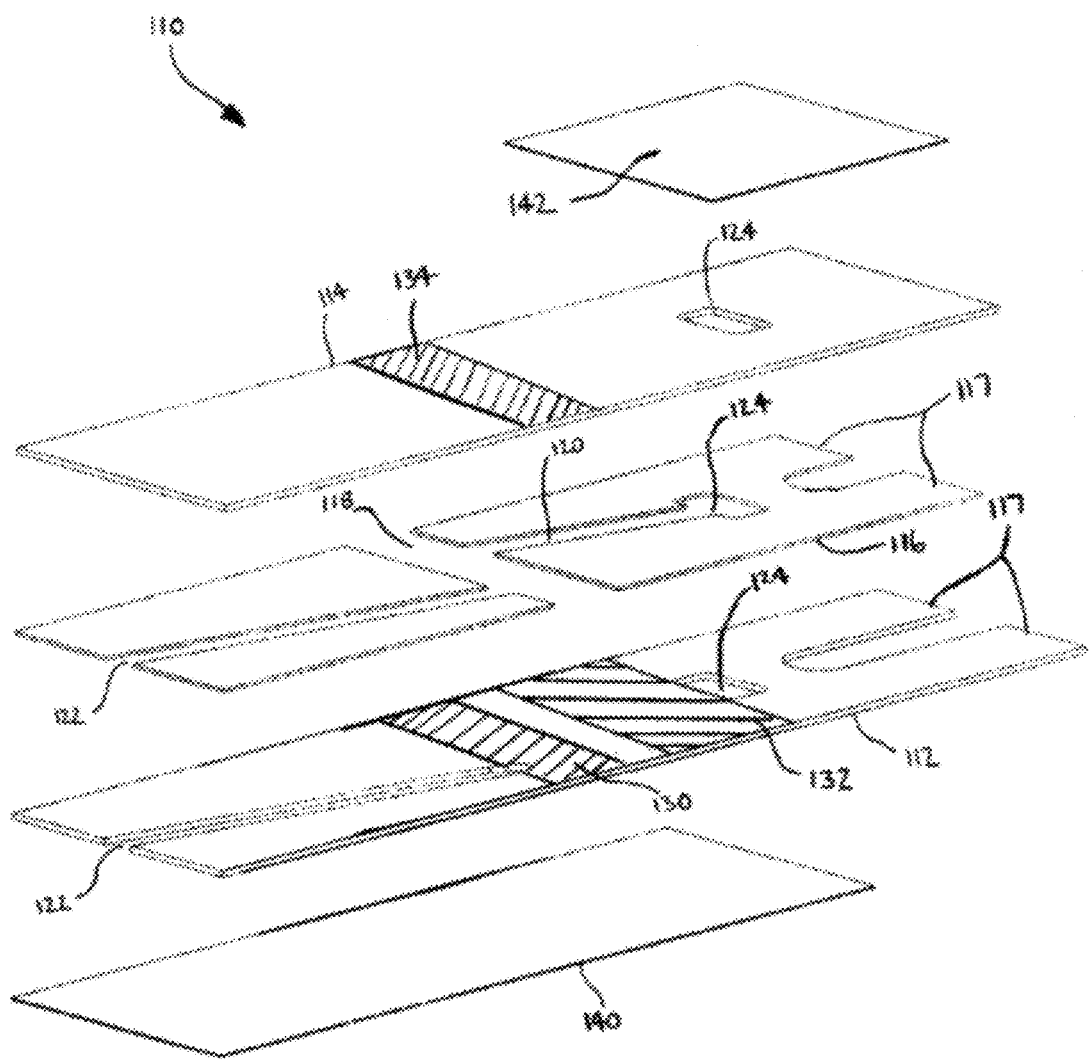
FIG. 6 illustrates an exploded view of an exemplary embodiment of an immunosensor in accordance with the present invention.

Another exemplary embodiment of a sample analyzing device for use in conjunction with at least some of the methods disclosed herein, an immunosensor 110, is illustrated in FIG. 6 and is described in U.S. patent application Ser. No. 12/570,268 of Chatelier et al., entitled "Adhesive Compositions for Use in an Immunosensor" and filed on Sep. 30, 2009, the contents of which is hereby incorporated by reference in its entirety. A plurality of chambers can be formed within the immunosensor, including a fill chamber, by which a sample can be introduced into the immunosensor, a reaction chamber, by which a sample can be reacted with one or more desired materials, and a detection chamber, by which a concentration of a particular component of the sample can be determined These chambers can be formed in at least a portion of a first electrode, a second electrode, and a separator of the immunosensor. The immunosensor can also include a vent hole to allow air to enter and escape the immunosensor as desired, and first and second sealing components to selectively seal first and second sides of the vent hole. The first sealing component can also form a wall of the fill chamber.

As illustrated, the immunosensor 110 includes a first electrode 112 having two liquid reagents 130, 132 striped onto it. The first electrode 112 can be formed using any number of techniques used to form electrodes, but in one embodiment a polyethylene terephthalate (PET) sheet that is filled with barium sulphate is sputter-coated with gold. The PET sheet can also be filled with titanium dioxide. Other non-limiting example of forming an electrode are disclosed in U.S. Pat. No. 6,521,110 of Hodges et al., entitled "Electrochemical Cell" and filed on Nov. 10, 2000, the contents of which is hereby incorporated by reference in its entirety.

Likewise, the liquid reagents 130, 132 can have a number of different compositions. In one embodiment the first liquid reagent 130 includes an antibody conjugated to an enzyme, such as GDH-PQQ, in a buffer that contains sucrose, as well as a poloxamer, such as Pluronics® block copolymers, an anticoagulant, such as citraconate, and calcium ions. In one embodiment the second liquid reagent 132 includes a mixture of ferricyanide, glucose, and a second mediator, such as phenazine ethosulfate, in an acidic buffer, such as a dilute citraconic acid solution. The first and second liquid reagents 130, 132 can be dried onto the first electrode 112. A number of techniques can be used to dry the reagents 130, 132, but in one embodiment, following the striping of the reagents 130, 132 on the first electrode 112, one or more infrared dryers can be applied to the reagents 130, 132. One or more air dryers can also be used, for example, subsequent to the infrared dryers. References to a first reagent and a first liquid reagent and a second reagent and a second liquid reagent herein are used interchangeably and are not necessarily an indication that the reagents are in their liquid or dried form at a given time for a particular embodiment. Further, some of the components associated with the first and second liquid reagents can be used interchangeably and/or in both the first and second liquid reagents as desired. By way of non-limiting example, an anticoagulant can be associated with either or both of the first liquid reagent 130 and the second liquid reagent 132.

A line can be formed in the sputter-coated gold between the reagents 130, 132 such that an edge of reagent 132 is very close to, or touches, the line. The line can be applied using laser ablation or with a sharp metal edge. In one exemplary embodiment the line can be applied before the reagents 130, 132 are striped on the electrode. The line can be designed to electrically insulate the section of the first electrode 112 under the detection chamber from the section that will be under the reaction chamber. This can provide a better definition of an area of the working electrode during the electrochemical assay.

The immunosensor 110 can also include an second electrode 114 having one or more magnetic beads 134 containing surface-bound antigens thereon. The antigens can be configured to react with the antibody disposed on the first electrode 112 and the sample within a reaction chamber 118, as described in further detail below. One skilled in the art will recognize that the components disposed on the first electrode 112 and on the second electrode 114 can be interchangeable. Thus, the first electrode 112 can include one or more magnetic beads 134 and the second electrode 114 can include two liquid reagents 130, 132 striped onto it. Further, although in the illustrated embodiment the length of the electrode 112 forms the length of the entire body of the immunosensor 110, in other embodiments the electrode can be only a portion of a layer of an immunosensor that serves as the first or second electrodes or multiple electrodes can be disposed on a single layer of an immunosensor. Further, because voltage applied to the immunosensor can be flipped and/or alternated, each of the first and second electrodes can serve as the working electrode and the counter or counter/reference electrode at different stages. For ease of description purposes, in the present application the first electrode is considered the working electrode and the second electrode the counter or counter/reference electrode.

A separator 116 disposed between the first and second electrodes 112, 114 can have a variety of shapes and sizes, but it generally is configured to desirably engage the first and second electrodes 112, 114 to form the immunosensor 110. In one exemplary embodiment, the separator 116 includes adhesive on both sides. The separator 116 can further include a release liner on each side of the two sides of the separator 116. The separator 116 can be cut in a manner that forms at least two cavities. A first cavity can be formed to serve as a reaction chamber 118 and a second cavity can be formed to serve as a detection chamber 120. In one embodiment, the separator 116 can be kiss-cut such that the reaction chamber 118 is aligned with the electrodes 112, 114 to allow an antigen-antibody reaction therein while the detection chamber 120 is aligned with the electrodes 112, 114 to allow for the electrochemical determination of ferrocyanide therein.

In one embodiment, the separator 116 can be placed on the first electrode 112 in a manner that allows the magnetic beads 134 of the second electrode 114 and the first reagent 130 of the first electrode 112 to be at least partially disposed in the reaction chamber 118 and the ferricyanide-glucose combination of the second reagent 132 of the first electrode 112 to be at least partially disposed in the detection chamber 120. It can be advantageous to include an anticoagulant in each of the first and second liquid reagents 130, 132 so that an anticoagulant is associated with each of the reaction and detection chambers 118, 120. In some embodiments the combination of one of the first and second electrodes 112, 114 and the separator 116 can be laminated together to form a bi-laminate, while in other embodiments the combination of each of the first electrode 112, the second electrode 114, and the separator 116 can be laminated together to form a tri-laminate. Alternatively, additional layers may also be added.

A fill chamber 122 can be formed by punching a hole into one of the first and second electrodes 112, 114 and the separator 116. In the illustrated embodiment the fill chamber is formed by punching a hole in the first electrode 112 and the separator 116 such that the hole in the first electrode 112 overlaps the reaction chamber 118. As shown, the fill chamber 122 can be a distance apart from the detection chamber 120. Such a configuration allows a sample to enter the immunosensor 110 through the fill chamber 122 and flow into the reaction chamber 118 to be reacted, for example with the first liquid reagent 130 that includes the antibody conjugated to an enzyme in a buffer on the first electrode 112 and the magnetic beads 134 striped on the second electrode 114, without entering the detection chamber 120. Once the sample has been reacted, it can then flow into the detection chamber 120 to undergo a chemical or physical transformation with the second liquid reagent 132, for example the mixture of ferricyanide, glucose, and the second mediator in an acidic buffer.

A vent 124 can be formed by punching a hole through each of the two electrodes 112, 114 and the separator 116 such that the vent 124 extends through the entirety of the immunosensor 110. The hole can be formed in a suitable manner, such as, for example, drilled or punched in a number of different locations, but in one exemplary embodiment it can overlap a region of the detection chamber 120 that is spaced apart from the reaction chamber 118.

The vent 124 can be sealed in a number of different manners. In the illustrated embodiment, a first sealing component 140 is located on the first electrode 112 to seal a first side of the vent 124 and a second sealing component 142 is located on the second electrode 114 to seal a second side of the vent 124. The sealing components can be made of and/or include any number of materials. By way of non-limiting example, either or both of the sealing components can be hydrophilic adhesive tape or Scotch® tape. Adhesive sides of the sealing components can face the immunosensor 110. As shown, not only can the first sealing component 140 form a seal for the vent 124, but it can also form a wall for the fill chamber 122 so that the sample can be contained therein. Properties incorporated onto the adhesive side of the first sealing component 140 can be associated with the fill chamber 122. For example, if the first sealing component 140 includes properties making it hydrophilic and/or water soluble, the fill chamber can remain well-wet when a sample is disposed therein. Further, the sealing components 140, 142 can be selectively associated and disassociated with the immunosensor 110 to provide venting and/or sealing for the immunosensor 110 and the components disposed therein as desired.

Adhesives can generally be used in the construction of the immunosensor. Non-limiting examples of ways in which adhesives can be incorporated into immunosensors and other sample analyzing devices of the present disclosure can be found in U.S. patent application Ser. No. 12/570,268 of Chatelier et al., entitled "Adhesive Compositions for Use in an Immunosensor" and filed on Sep. 30, 2009, the contents of which was already incorporated by reference in its entirety.

While the present disclosure discusses a variety of different embodiments related to immunosensors, other embodiments of immunosensors can also be used with the methods of the present disclosure. Non-limiting examples of such embodiments include those described in U.S. Patent Application Publication No. 2003/0180814 of Hodges et al., entitled "Direct Immunosensor Assay" and filed on Mar. 21, 2002, U.S. Patent Application Publication No. 2004/0203137 of Hodges et al., entitled "Immunosensor" and filed on Apr. 22, 2004, U.S. Patent Application Publication No. 2006/0134713 of Rylatt et al., entitled "Biosensor Apparatus and Methods of Use" and filed on Nov. 21, 2005, and U.S. patent application Ser. No. 12/563,091, which claims priority to each of U.S. Patent Application Publication Nos. 2003/0180814 and 2004/0203137, each of which is hereby incorporated by reference in its entirety.

In one embodiment, the immunosensor 110 can be configured to be placed into a meter that is configured, e.g., via a suitable circuit, to apply a potential to the electrodes 112, 114 and measure a current that results from the application of the potential. In one embodiment, the immunosensor includes one or more tabs 117 for engaging a meter. Other features can also be used to engage the immunosensor 110 with a meter. The meter can include a number of different features. For example, the meter can include a magnet that is configured to maintain certain components of the immunosensor 110 in one chamber while other components flow to the other. In one exemplary embodiment, the magnet of the meter is located such that, upon placing the immunosensor 110 in the meter, the magnet is disposed below the reaction chamber 118. This can allow the magnet to assist in holding back any magnetic beads 134, and more particularly any antibody-enzyme conjugate that is bound to the beads 134, from flowing into the detection chamber 120.

An alternate feature of the meter includes a heating element. A heating element can help speed up the reaction rate and help the sample flow through the immunosensor 110 in a desired manner by reducing the viscosity. A heating element can also allow one or more chambers and/or a sample disposed therein to be heated to a predetermined temperature. Heating to a predetermined temperature can help provide accuracy, for example, by diminishing or removing the effects of temperature change as reactions occur.

Further, a piercing instrument can also be associated with the meter. The piercing instrument can be configured to pierce at least one of the first and second sealing components at a desired time so that air can flow out of the vent hole and liquid can flow from the reaction chamber into the detection chamber.

The immunosensor 110 and the test strip 62 can also be configured to be associated with a control unit. The control unit can be configured to perform a variety of functions. In one exemplary embodiment, the control unit is capable of measuring a fill time of a sample when it is introduced to the device. In another embodiment, the control unit can be configured to determine a haematocrit value of a blood sample. In yet another embodiment, the control unit can is configured to calculate a concentration of an analyte in the sample in view of the fill time. In fact, the control unit can include a number of different features, depending, at least in part, on the functionality desired and the method by which the system is designed to measure the fill time.

The control unit can also measure other aspects of the system. By way of non-limiting example, the control unit can be configured to measure a temperature of one or more chambers of the immunosensor or test strip. It can also be configured to measure a temperature of the sample, a color of the sample, a capacitance of the immunosensor or test strip or a variety of other characteristics and/or properties of the sample and/or the system. By way of further non-limiting example, the control unit can be configured to communicate the results of the fill time determination, the results of the capacitance measurement, the results of the analyte concentration determination, and/or the haematocrit measurement to outside equipment. This can be accomplished in any number of ways. In one embodiment, the control unit can be hardwired to a microprocessor and/or a display device. In another embodiment, the control unit can be configured to wirelessly transmit data from the control unit to a microprocessor and/or a display device.

Other components of the system can also be configured to make such measurements. For example, the immunosensor or the meter can be configured to measure a temperature of one or more chambers of the immunosensor or test strip, measure or infer the temperature of a sample, or measure, determine, or infer a variety of other characteristics and/or properties of the sample and/or the system. Still further, one skilled in the art will recognize that these features of a control unit can be interchanged and selectively combined in a single control unit. For example, a control unit can both determine a fill time, a capacitance, and measure a temperature of a chamber. In other embodiments, multiple control units can be used together to perform various functions, based at least in part on the configurations of the various control units and the desired functions to be performed.

Analyte Concentration Test

Figure 7A:
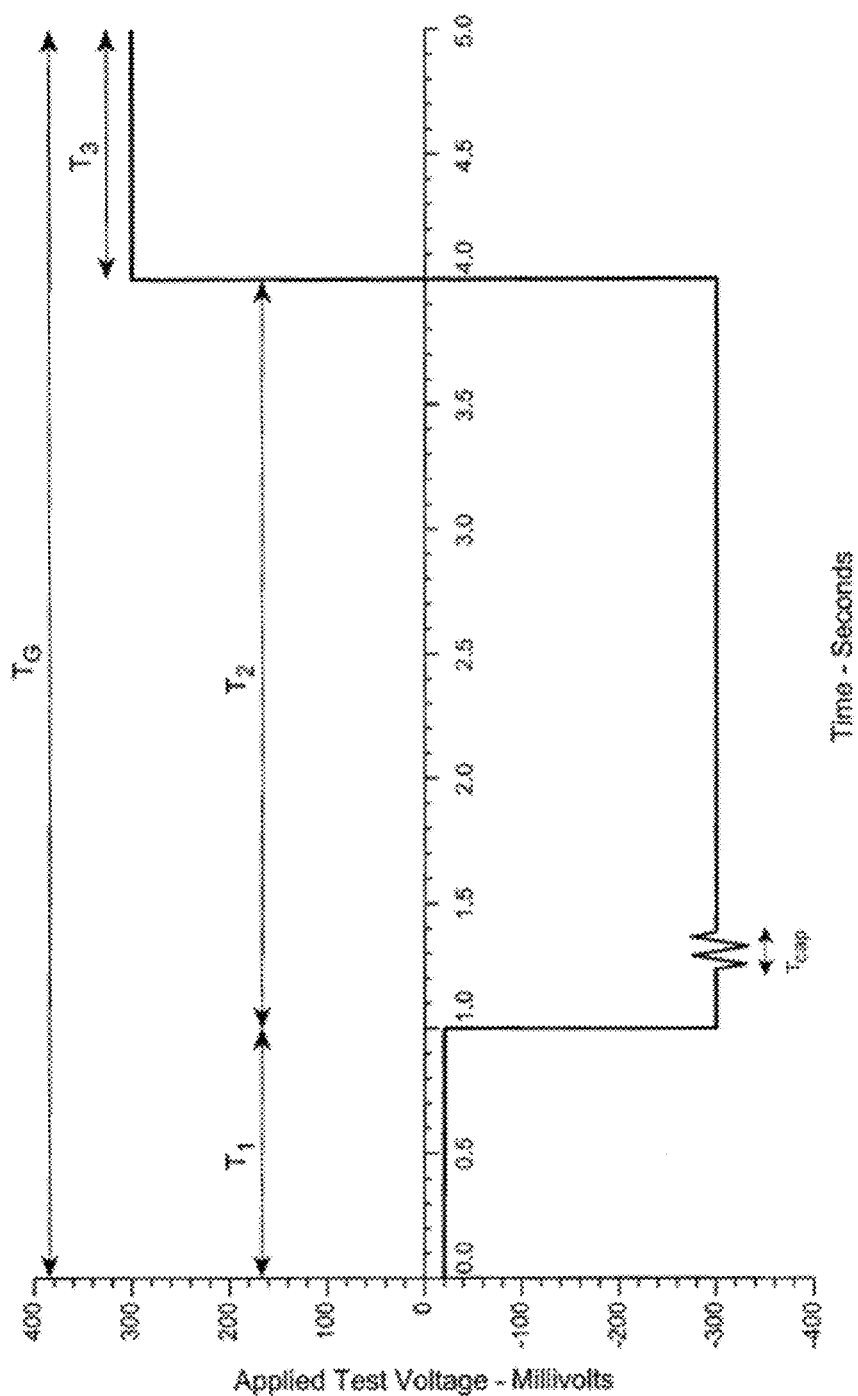
FIG. 7A illustrates a test voltage waveform in which the test meter applies a plurality of test voltages for prescribed time intervals.

In one embodiment, once the test meter 100 has determined that a fluid has been introduced (e.g., dosed) onto the test strip 62, a test meter 100 can perform a glucose test by applying a plurality of test potentials to the test strip 62 for prescribed intervals as shown in FIG. 7A. A glucose test time interval $T_G$ represents an amount of time to perform the glucose test (but not necessarily all the calculations associated with the glucose test) where the glucose test time interval $T_G$ can include a first test potential $E_1$ for a first test potential time interval $T_1$, a second test potential $E_2$ for a second test potential time interval $T_2$, and a third test potential $E_3$ for a third test potential time interval $T_3$. Further, as illustrated in FIG. 7A, the second test potential time interval $T_2$ can include a constant (DC) test voltage component and a superimposed alternating (AC), or oscillating, test voltage component. The superimposed alternating test voltage component can be applied for a time interval indicated by $T_{cap}$. The glucose test time interval $T_G$ can range, for example, from about 1 second to about 5 seconds.

As discussed above, either the first electrode 166 or the second electrode 164 can function as working electrode which oxidizes or reduces a limiting amount of mediator depending on the polarity of the applied test potential of the test meter. It should be noted that unless otherwise stated all potentials applied by test meter 100 will hereinafter be stated with respect to second electrode 164. However, applicants note that the test potentials applied by test meter 100 can also be stated with respect to the first electrode 166, in which case the polarity of the test potentials and measured currents discussed below would be reversed.

The plurality of test current values measured during the first, second, and third test potential time intervals may be performed at a frequency ranging from about 1 measurement per approximately 1 nanosecond to about one measurement per approximately 100 milliseconds. Applicants note that names "first," "second," and "third" are chosen for convenience and do not necessarily reflect the order in which the test potentials are applied. For instance, an embodiment can have a potential waveform where the third test voltage can be applied before the application of the first and second test voltage. While an embodiment using three test voltages in a serial manner is described, applicants note that the glucose test can include different numbers of open-circuit and test voltages. Applicants note that the glucose test time interval can include any number open-circuit potential time intervals. For example, the glucose test time interval could include only two test potential time intervals and/or open circuit potential time intervals before and/or after one or more test potential time intervals. In another exemplary embodiment, the glucose test could include an open-circuit for a first time interval, a second test voltage for a second time interval, and a third test voltage for a third time interval.

As shown in FIG. 7A, the test meter 100 may apply a first test potential $E_1$ (e.g., about −20 mV as illustrated in FIG. 7A) for a first test potential time interval $T_1$ (e.g., in the range of about 0 to about 1 second). The first test potential time interval $T_1$ can range from about 0.1 seconds to about 3 seconds and preferably range from about 0.2 seconds to about 2 seconds, and most preferably range from about 0.3 seconds to about 1 seconds from an initiation point of zero (0) seconds in FIG. 7A. The first test potential time interval $T_1$ may be sufficiently long so that the sample reaction chamber 61 can fully fill with sample and also so that the reagent layer 72 can at least partially dissolve or solvate. In other embodiments, the first test potential time interval $T_1$ can include any other desired time ranges.

In one embodiment, the test meter 100 can apply a first test potential $E_1$ between the electrodes for a duration between when the meter can detect that the strip is filling with sample and before a second test potential $E_2$ is applied. In one aspect, the test potential $E_1$ is small. For example, the potential can be in the range of about −1 to about −100 mV, preferably in the range of about −5 mV to about −50 mV and most preferably in the range of about −10 mV to about −30 mV. The smaller potential perturbs the reduced mediator concentration gradient to a lesser extent compared to applying a larger potential difference, but is still sufficient to obtain a measure of the oxidizable substances in the sample. The test potential $E_1$ can be applied for a portion of the time between detection of fill and when the second test potential $E_2$ is applied or can be applied for the whole of that time period. If the test potential $E_1$ is to be used for a portion of the time then an open-circuit could be applied for the remaining portion of the time. The combination of any number of open-circuit and small voltage potential applications, their order and times applied is not critical in this embodiment, can be applied as long as the total period for which the small potential $E_1$ is applied is sufficient to obtain a current measurement indicative of the presence and/or quantity of oxidizable substances present in the sample. In a preferred embodiment, the small potential $E_1$ is applied for substantially the entire period between when a fill is detected and when the second test potential $E_2$ is applied.

During the first time interval $T_1$, the test meter 100 measures the resulting first current transient, which can be referred to as $i_a(t)$. A current transient represents a plurality of current values measured by a test meter during a particular test potential time interval. The first current transient can be an integral of current values over the first test potential time interval, or an average or single current value measured during the first test potential time interval multiplied by the time interval of the first test potential time interval. In some embodiments, the first current transient can include current values measured over various time intervals during the first test potential time interval. In one embodiment, the first current transient $i_a(t)$ can be measured for a time in the range of about 0.05 seconds to about 1.0 second and preferably in the range of about 0.1 seconds to about 0.5 seconds, and most preferably in the range of about 0.1 seconds to about 0.2 seconds. In other embodiments, the first current transient $i_a(t)$ can be measured for other desired time ranges. As discussed below, a portion or all of the first current transient can be used in the methods described herein to determine whether a control solution or a blood sample was applied to the test strip 62. The magnitude of the first transient current is affected by the presence of easily oxidizable substances in the sample. Blood usually contains endogenous and exogenous compounds that are easily oxidized at second electrode 164. Conversely, the control solution can be formulated such that it does not contain oxidizable compounds. However, blood sample composition can vary and the magnitude of the first current transient for high viscosity blood samples will typically be smaller than low viscosity samples (in some cases even less than the control solution samples) because the sample reaction chamber 61 may be not be completely filled after about 0.2 seconds. An incomplete fill will cause the effective area of the first electrode 166 and the second electrode 164 to decrease which in turn can cause the first current transient to decrease. Thus, the presence of oxidizable substances in a sample, by itself, is not always a sufficient discriminatory factor because of variations in blood samples.

Once the first time interval $T_1$ time has elapsed, the test meter 100 can apply a second test potential $E_2$ between the first electrode 166 and the second electrode 164 (e.g., about −300 mV as illustrated in FIG. 7A) for a second test potential time interval $T_2$ (e.g., about 3 seconds as illustrated in FIG. 7A). The second test potential $E_2$ may be a value sufficiently negative of the mediator redox potential so that a limiting oxidation current occurs at the second electrode 164. For example, when using ferricyanide and/or ferrocyanide as the mediator, the second test potential $E_2$ can range from about −600 mV to about zero mV, preferably range from about −600 mV to about −100 mV, and more preferably be about −300 mV. Likewise, the time interval indicated as $t_{cap}$ in FIG. 6 may also last over a range of times, but in one exemplary embodiment it has a duration of about 20 milliseconds. In one exemplary embodiment, the superimposed alternating test voltage component is applied after about 0.3 seconds to about 0.32 seconds after the application of the second test voltage $V_2$, and induces two cycles of a sine wave having a frequency of about 109 Hz with an amplitude of about +/−50 mV. During the second test potential time interval $T_2$, the test meter 100 can measure a second current transient $i_b(t)$.

The second test potential time interval $T_2$ may be sufficiently long to monitor the rate of generation of reduced mediator (e.g., ferrocyanide) in the sample reaction chamber 61 based on the magnitude of a limiting oxidation current. The reduced mediator may be generated by a series of chemical reactions in the reagent layer 72. During the second test potential time interval $T_2$, a limiting amount of reduced mediator is oxidized at the second electrode 164 and a non-limiting amount of oxidized mediator is reduced at the first electrode 166 to form a concentration gradient between the first electrode 166 and the second electrode 164. As will be described, the second test potential time interval $T_2$ should be sufficiently long so that a sufficient amount of ferricyanide can be generated at the second electrode 164. A sufficient amount of ferricyanide may be required at the second electrode 164 so that a limiting current can be measured for oxidizing ferrocyanide at the first electrode 166 during the third test potential $E_3$. The second test potential time interval $T_2$ can range from about 0 seconds to about 60 seconds and preferably range from about 1 second to about 10 seconds, and most preferably range from about 2 seconds to about 5 seconds.

Figure 7B:
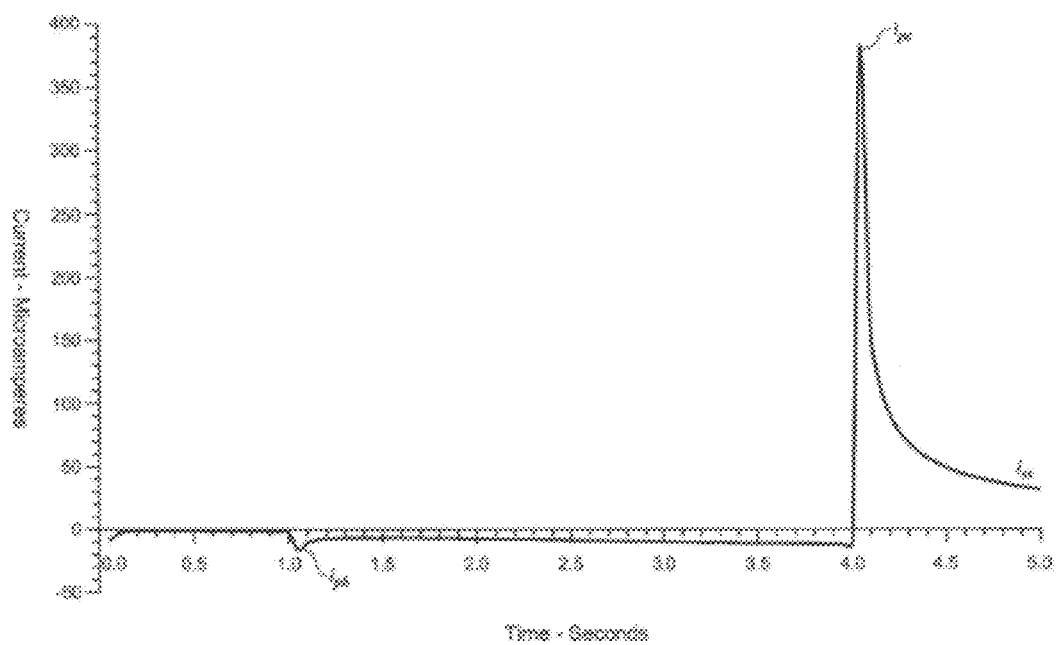
FIG. 7B illustrates a test current transient generated with the test voltage waveform of FIG. 6.

FIG. 7B shows a relatively small peak $i_{pb}$ at the beginning of the second test potential time interval $T_2$ followed by a gradual increase of an absolute value of an oxidation current during the second test potential time interval (e.g., in the range of about 1 second to about 4 seconds). The small peak occurs due to an initial depletion of reduced mediator at about 1 second. The gradual increase in oxidation current is ascribed to the generation of ferrocyanide by reagent layer 72 followed by its diffusion to the second electrode 164.

After the second potential time interval $T_2$ has elapsed, the test meter 100 can apply a third test potential $E_3$ between the first electrode 166 and the second electrode 164 (e.g., about +300 mV as illustrated in FIG. 7A) for a third test potential time interval $T_3$ (e.g., in the range of about 4 to about 5 seconds as illustrated in FIG. 6). During the third test potential time interval $T_3$, the test meter 100 can measure a third current transient, which may be referred to as $i_c(t)$. The third test potential $E_3$ may be a value sufficiently positive of the mediator redox potential so that a limiting oxidation current is measured at the first electrode 166. For example, when using ferricyanide and/or ferrocyanide as the mediator, the magnitude of the third test potential $E_3$ can range from about zero mV to about 600 mV, preferably range from about 100 mV to about 600 mV, and more preferably be about 300 mV.

The second test potential time interval $T_2$ and the third test potential time interval $T_3$ can each range from about 0.1 seconds to about 4 seconds. For the embodiment shown in FIG. 7A, the second test potential time interval $T_2$ was about 3 seconds and the third test potential time interval $T_3$ was about 1 second. As mentioned above, an open circuit potential time period can be allowed to elapse between the second test potential $E_2$ and the third test potential $E_3$. Alternatively, the third test potential $E_3$ can be applied following the application of the second test potential $E_2$. Note that a portion of the first, second, or third current transient may be generally referred to as a cell current or a current value.

The third test potential time interval $T_3$ may be sufficiently long to monitor the diffusion of a reduced mediator (e.g., ferrocyanide) near the first electrode 166 based on the magnitude of the oxidation current. During the third test potential time interval $T_3$, a limiting amount of reduced mediator is oxidized at the first electrode 166 and a non-limiting amount of oxidized mediator is reduced at the second electrode 164. The third test potential time interval $T_3$ can range from about 0.1 seconds to about 5 seconds and preferably range from about 0.3 seconds to about 3 seconds, and most preferably range from about 0.5 seconds to about 2 seconds.

FIG. 7B shows a relatively large peak $i_{pc}$ at the beginning of the third test potential time interval $T_3$ followed by a decrease to a steady-state current. In one embodiment, the first test potential $E_1$ and the second test potential $E_2$ both have a first polarity, and the third test potential $E_3$ has a second polarity, which is opposite to the first polarity. However, applicants note that the polarity of the first, second, and third test potentials can be chosen depending on the manner in which analyte concentration is determined and/or depending on the manner in which the test samples and control solutions are distinguished.

Capacitance Measurement

In some embodiments, a capacitance can be measured. The capacitance measurement can measure essentially an ionic double-layer capacitance resulting from the formation of ionic layers at the electrode-liquid interface. A magnitude of the capacitance can be used to determine whether a sample is control solution or a blood sample. For example, when a control solution is within the reaction chamber, the magnitude of the measured capacitance can be greater than the magnitude of the measured capacitance when a blood sample is in the reaction chamber. As will be discussed in more detail below, a measured capacitance can be used in various methods to correct for the effects of changes in a physical property of the electrochemical cell on measurements made using the electrochemical cell. For example, changes in the measured capacitance can be related to at least one of an age of the electrochemical cell and a storage condition of the electrochemical cell.

By way of non-limiting example, methods and mechanisms for performing capacitance measurements on test strips can be found in U.S. Pat. Nos. 7,195,704 and 7,199,594, each of which is hereby incorporated by reference in its entirety. In one exemplary method for measuring capacitance, a test voltage having a constant component and an oscillating component is applied to the test strip. In such an instance, the resulting test current can be mathematically processed, as described in further detail below, to determine a capacitance value.

Generally, when a limiting test current occurs at a working electrode having a well-defined area (i.e., an area not changing during the capacitance measurement), the most accurate and precise capacitance measurements in an electrochemical test strip can be performed. A well-defined electrode area that does not change with time can occur when there is a tight seal between the electrode and the spacer. The test current is relatively constant when the current is not changing rapidly due either to glucose oxidation or electrochemical decay. Alternatively, any period of time when an increase in signal, which would be seen due to glucose oxidation, is effectively balanced by a decrease in signal, which accompanies electrochemical decay, can also be an appropriate time interval for measuring capacitance.

An area of first electrode 166 can potentially change with time after dosing with the sample if the sample seeps in between the spacer 60 and the first electrode 166. In an embodiment of a test strip, reagent layer 72 can be have an area larger than the cutout area 68 that causes a portion of the reagent layer 72 to be in between the spacer 60 and the first electrode layer 66. Under certain circumstances, interposing a portion of the reagent layer 72 in between the spacer 60 and the first electrode layer 66 can allow the wetted electrode area to increase during a test. As a result, a leakage can occur during a test that causes the area of the first electrode to increase with time, which in turn can distort a capacitance measurement.

In contrast, an area of second electrode 164 can be more stable with time compared to the first electrode 166 because there is no reagent layer in between the second electrode 164 and the spacer 60. Thus, the sample is less likely to seep in between the spacer 60 and the second electrode 164. A capacitance measurement that uses a limiting test current at the second electrode 164 can thus be more precise because the area does not change during the test.

As discussed above and as shown in FIG. 7A, once liquid is detected in the test strip, first test potential $E_1$ (e.g., about $-20$ mV, as illustrated in FIG. 7A) can be applied between the electrodes for about 1 second to monitor the fill behavior of the liquid and to distinguish between control solution and blood. In Equation 1, the test currents are used from about 0.05 to about 1 second. This first test potential $E_1$ can be relatively low such that the distribution of ferrocyanide in the cell is disturbed as little as possible by the electrochemical reactions occurring at the first and second electrodes.

A second test potential $E_2$ (e.g., about $-300$ mV, as illustrated in FIG. 7A) having a larger absolute magnitude can be applied after the first test potential $E_1$ such that a limiting current can be measured at the second electrode 164. The second test potential $E_2$ can include an AC voltage component and a DC voltage component. The AC voltage component can be applied at a predetermined amount of time after the application of the second test potential $E_2$, and further, can be a sine wave having a frequency of about 109 Hertz and an amplitude of about +/−50 millivolts. In a preferred embodiment, the predetermined amount of time can range from about 0.3 seconds to about 0.4 seconds after the application of the second test potential $E_2$. Alternatively, the predetermined amount of time can be a time where a test current transient as a function of time has a slope of about zero. In another embodiment, the predetermined amount of time can be a time required for a peak current value (e.g., $i_{pb}$) to decay by about 50%. As for the DC voltage component, it can be applied at a beginning of the first test potential. The DC voltage component can have a magnitude sufficient to cause a limiting test current at the second electrode such as, for example, about $-300$ mV with respect to the second electrode.

Figure 4B:
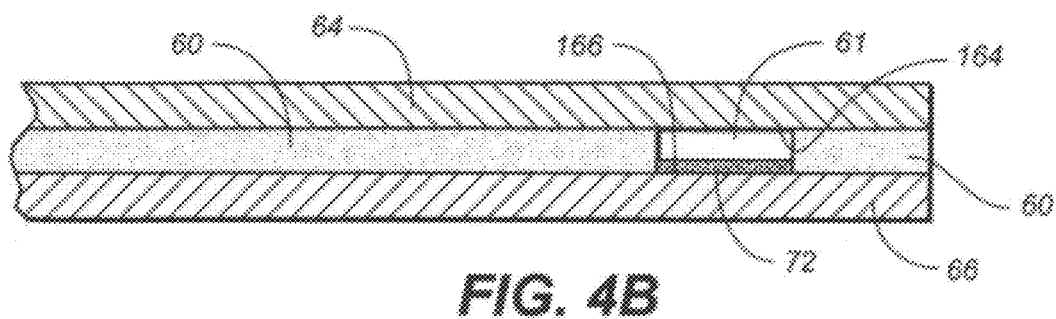
FIG. 4B illustrates a partial side view of the distal portion of the test strip consistent with arrows 4B-4B of FIG. 4A.

Consistent with FIG. 4B, the reagent layer 72 is not coated onto the second electrode 164, which causes the magnitude of the absolute peak current $i_{pb}$ to be relatively low compared to the magnitude of the absolute peak current $i_{pc}$. The reagent layer 72 can be configured to generate a reduced mediator in a presence of an analyte, and the amount of the reduced mediator proximate to first electrode can contribute to the relatively high absolute peak current $i_{pc}$. In one embodiment at least the enzyme portion of the reagent layer 72 can be configured to not substantially diffuse from the first electrode to the second electrode when a sample is introduced into the test strip.

The test currents after $i_{pb}$ tends to settle to a flat region at approximately 1.3 seconds, and then the current increases again as the reduced mediator generated at the first electrode 166, which can be coated with the reagent layer 72, diffuses to the second electrode 164, which is not coated with the reagent layer 72. In one embodiment, a capacitance measurement can be performed at a relatively flat region of the test current values, which can be performed at about 1.3 seconds to about 1.4 seconds. Generally, if the capacitance is measured before 1 second, then the capacitance measurement can interfere with the relatively low first test potential $E_1$ that can be used to measure the first current transient $i_a(t)$. For example, an oscillating voltage component on the order of $\pm 50$ mV superimposed onto a $-20$ mV constant voltage component can cause significant perturbation of the measured test current. Not only does the oscillating voltage component interfere with the first test potential $E_1$, but it can also significantly perturb the test currents measured at about 1.1 seconds, which in turn can interfere with correction for antioxidants. Following a great deal of testing and experimentation, it was finally determined that, surprisingly, measuring the capacitance at about 1.3 seconds to about 1.4 seconds resulted in accurate and precise measurements that did not interfere with the control solution/blood discrimination test or the blood glucose algorithm.

After the second test potential $E_2$, third test potential $E_3$ (e.g., about +300 mV, as illustrated in FIG. 7A) can be applied causing the test current to be measured at the first electrode 166, which can be coated with the reagent layer 72. The presence of a reagent layer on the first electrode can allow penetration of liquid between the spacer layer and the electrode layer, which can cause the electrode area to increase.

As illustrated in FIG. 7A, in an exemplary embodiment a 109 Hz AC test voltage ($\pm 50$ mV peak-to-peak) can be applied for 2 cycles during the time interval $t_{cap}$. The first cycle can be used as a conditioning pulse and the second cycle can be used to determine the capacitance. The capacitance estimate can be obtained by summing the test current over a portion of the alternating current (AC) wave, subtracting the direct current (DC) offset, and normalizing the result using the AC test voltage amplitude and the AC frequency. This calculation provides a measurement of the capacitance of the strip, which is dominated by the strip sample chamber when it is filled with a sample.

In one embodiment the capacitance can be measured by summing the test current over one quarter of the AC wave on either side of the point in time where the input AC voltage crosses the DC offset, i.e. when the AC component of the input voltage is zero (the zero crossing point). A derivation of how this translates to a measurement of the capacitance is described in further detail below. Equation 1 can show the test current magnitude as a function of time during the time interval $t_{cap}$:

$$i(t) = i_o + st + I\sin(\omega t + \phi) \qquad \text{Eq. 1}$$

where the terms $i_o + st$ represent the test current caused by the constant test voltage component. Generally, the DC current component is considered as changing linearly with time (due to the on-going glucose reaction generating ferrocyanide) and is thus represented by a constant $i_o$, which is the DC current at time zero (the zero crossing point), and s, the slope of the DC current change with time. The AC current component is represented by $I\sin(\omega t + \phi)$, where I is the amplitude of the current wave, $\omega$ is its frequency, and $\phi$ is its phase shift relative to the input voltage wave. The term $\omega$ can also be expressed as $2\pi f$, where f is the frequency of the AC wave in Hertz. The term I can also be expressed as shown in Equation 2:

$$I = \frac{V}{|Z|} \qquad \text{Eq. 2}$$

where V is the amplitude of the applied voltage signal and $|Z|$ is the magnitude of the complex impedance. The term $|Z|$ can also be expressed as shown in Equation 22:

$$|Z| = \frac{R}{\sqrt{1+\tan^2\phi}} = \frac{R}{\sqrt{1+\omega^2 R^2 C^2}} \qquad \text{Eq. 3}$$

where R is the real part of the impedance and C is the capacitance.

Equation 1 can be integrated from one quarter wavelength before the zero crossing point to one quarter wavelength after the zero crossing point to yield Equation 4:

$$\int_{-1/4f}^{1/4f} i(t) = i_o[t]_{-1/4f}^{1/4f} + \frac{S}{2}[t^2]_{-1/4f}^{1/4f} + I\int_{-1/4f}^{1/4f} \sin(\omega t + \phi), \qquad \text{Eq. 4}$$

which can be simplified to Equation 5:

$$\int_{-1/4f}^{1/4f} i(t) = \frac{i_o}{2f} + \frac{I\sin\phi}{\pi f}. \qquad \text{Eq. 5}$$

By substituting Eq. 2 into Eq. 1, then into Eq. 4, and then rearranging, Equation 6 results:

$$C = \frac{1}{2V}\left(\int_{-1/4f}^{1/4f} i(t) - \frac{i_o}{2f}\right). \qquad \text{Eq. 6}$$

The integral term in Equation 6 can be approximated using a sum of currents shown in an Equation 7:

$$\int_{-1/4f}^{1/4f} i(t) \approx \frac{\frac{1}{n}\sum_{k=1}^{n} i_k}{2f} \qquad \text{Eq. 7}$$

where the test currents $i_k$ are summed from one quarter wavelength before the zero crossing point to one quarter wavelength past the zero crossing point. Substituting Equation 7 into Equation 6 yields Equation 8:

$$C = \frac{\frac{1}{n}\sum_{k=1}^{n} i_k - i_o}{4Vf}, \qquad \text{Eq. 8}$$

in which the DC offset current $i_o$ can be obtained by averaging the test current over one full sine cycle around the zero crossing point.

In another embodiment, the capacitance measurements can be obtained by summing the currents not around the voltage zero crossing point, but rather around the maximum AC component of the current. Thus, in Equation 7, rather than sum a quarter wavelength on either side of the voltage zero crossing point, the test current can be summed a quarter wavelength around the current maximum. This is tantamount to assuming that the circuit element responding to the AC excitation is a pure capacitor, so $\phi$ is $\pi/2$. Thus, Equation 5 can be reduced to Equation 9:

$$\int_{-1/4f}^{1/4f} i(t) = \frac{i_o}{2f} + \frac{I}{\pi f}. \qquad \text{Eq. 9}$$

This is believed to be a reasonable assumption in this case as the uncoated electrode is polarized such that the DC, or real, component of the current flowing is independent of the voltage applied over the range of voltages used in the AC excitation. Accordingly, the real part of the impedance responding to the AC excitation is infinite, implying a pure capacitive element. Equation 9 can then be used with Equation 6 to yield a simplified capacitance equation that does not require an integral approximation. The net result is that capacitance measurements when summing the currents not around the voltage crossing point, but rather around the maximum AC component of the current, were more precise.

CS/Blood Discrimination Test

In some embodiments, a control solution (CS)/blood discrimination test can be performed. If the CS/blood discrimination test determines that the sample is blood, then a series of steps can be performed that can include: the application of a blood glucose algorithm, hematocrit correction, blood temperature correction, and error checks; and if the CS/blood discrimination test determines that the sample is CS (i.e., not blood), then a series of steps can be performed that can include: the application of a CS glucose algorithm, CS temperature correction, and error checks. If there are no errors, then the test meter outputs a glucose concentration, but if there are errors, then the test can output an error message.

In one embodiment, characteristics of a control solution (CS) are used to distinguish control solutions from blood. For example, the presence and/or concentration of redox species in the sample, reaction kinetics, and/or capacitance can be used to distinguish control solutions from blood. The method disclosed herein can include the step of calculating a first reference value that is representative of the redox concentration in the sample and a second reference value that is representative of the rate of reaction of the sample with the reagent. In one embodiment, the first reference value is an interferent oxidation current and the second reference value is a reaction completion index.

In one embodiment, a CS/blood discrimination test can include a first reference value and a second reference value. The first value can be calculated based on the current values within the first time interval $T_1$ and the second reference value can be based on current values during both the second time interval $T_2$ and the third time interval $T_3$. In one embodiment the first reference value can be obtained by performing a summation of the current values obtained during the first time current transient when using the test voltage waveform of FIG. 7A. By way of non-limiting example, a first reference value $i_{sum}$ can be represented by Equation 10:

$$i_{sum} = \sum_{t=0.05}^{1} i(t) \qquad \text{Eq. 10}$$

where the term $i_{sum}$ is the summation of current values and t is a time. The second reference value, sometimes referred to as the residual reaction index, can be obtained by a ratio Y of current values during the second time interval and the third time interval, as shown in Eq. 11:

$$Y = \text{abs}\left(\frac{i(3.8)}{i(4.15)}\right) \qquad \text{Eq. 11}$$

where abs represents an absolute value function and 3.8 and 4.15 represent the time in seconds of the second and third time intervals, respectively, for this particular example.

A discrimination criterion can be used to determine if the sample is either control solution or blood based on the first reference value of Eq. 10 and the second reference of Eq. 11. For example, the first reference value of Eq. 10 can be compared to a pre-determined threshold and the second reference value of Eq. 11 can be compared to a pre-determined threshold function. The pre-determined threshold may be, for example, about 12 microamperes. The pre-determined threshold function can be based on a function using the first reference value of Eq. 10. More specifically, as illustrated by Eq. 12, where the calculated value of either of $i_{sum}$ in Eq. 10 is represented by X, the pre-determined threshold function $F_{pdt}$ can be:

$$F_{PDT} = Z\frac{X-12}{X} \qquad \text{Eq. 12}$$

where Z can be a constant such as, for example, about 0.2. Thus, the CS/Blood discrimination test can identify a sample as blood if $i_{sum}$, as shown in Eq. 10, is greater than or equal to the predetermined threshold, e.g., about 12 microamperes, and if the ratio Y of current values during the second time interval and the third time interval, as shown in Eq. 11, is less than the value of the pre-determined threshold function $F_{pdt}$, else the sample is a control solution.

Blood Glucose Algorithm

Figure 8A:
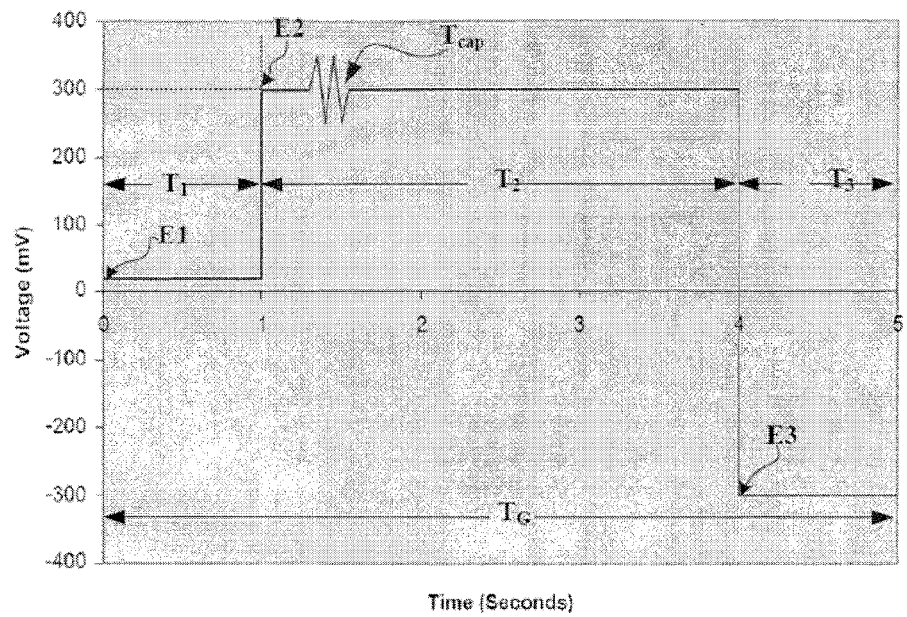
FIG. 8A illustrates a test voltage waveform in which the test meter applies a plurality of test voltages at opposite polarity for prescribed time intervals as compared to FIG. 7A.

If the sample is identified as a blood sample, a blood glucose algorithm can be performed on the test current values. Assuming that a test strip has an opposing face or facing arrangement as shown in FIGS. 1A-4B, and that a potential waveform is applied to the test strip as shown in FIG. 7A or FIG. 8A, a glucose concentration [G] can be calculated using a glucose algorithm as shown in Equation (Eq.) 13:

$$[G] = \left(\frac{|i_2|}{|i_3|}\right)^p (a|i_1| - Z) \qquad \text{Eq. 13}$$

In Eq. 13, [G] is the glucose concentration, $i_1$ is a first current value, $i_2$ is a second current value, and $i_3$ is a third current value, and the terms p, Z, and a are empirically derived calibration constants. A derivation of Eq. 13 can be found in a pending U.S. Published Patent Application No. 2007/0074977 (U.S. application Ser. No. 11/240,797), filed on Sep. 30, 2005 and entitled "Method and Apparatus for Rapid Electrochemical Analysis," the entirety of which is hereby incorporated herein by reference. All test current values (e.g., $i_1$, $i_2$, and $i_3$) in Equation 13 use the absolute value of the current. The first current value $i_1$ and the second current value $i_2$ are calculated from the third current transient and the third current value $i_3$ is calculated from the second current transient. Applicants note that the names "first," "second," and "third" are chosen for convenience and do not necessarily reflect the order in which the current values are calculated. In addition, all current values (e.g., $i_1$, $i_2$, and $i_3$) stated in Eq. 13 use the absolute value of the current. In an embodiment, $i_2$ may be based on one or more current values collected during the third current transient and $i_3$ may be based on one or more current values collected during the second current transient. In another embodiment, $i_2$ may be based on one or more current values collected at about the end of the third current transient and $i_3$ may be based on one or more current values collected at about the beginning of the second current transient. Both $i_2$ and $i_3$ may be calculated using a summation, integration, or an average for a portion of the respective time intervals.

In another embodiment, the term $i_1$ can be defined to include peak current values from the second and third current transients to allow for more accurate glucose concentration as shown in Eq. 14:

$$i_1 = i_2\left\{\frac{i_{pc} - 2i_{pb} + i_{ss}}{i_{pc} + i_{ss}}\right\} \qquad \text{Eq. 14}$$

The term $i_{pb}$ represents a peak current value for the second test potential time interval $T_2$ and the $i_{pc}$ term represents a peak current value for the third test potential time interval $T_3$. The term $i_{ss}$ is an estimate of the steady-state current, which is the current predicted to occur at long times after the application of the third test potential $E_3$ in the absence of on-going chemical reactions. Some examples of methods for calculating $i_{ss}$ can be found in U.S. Pat. Nos. 5,942,102 and 6,413,410, each of which is hereby incorporated by reference in its entirety. The use of peak current values to account for interferents in a physiological sample are described in U.S. Published Patent Application No. 2007/0227912 (U.S. patent application Ser. No. 11/278,341), filed on Mar. 31, 2006 and entitled "Methods and Apparatus for Analyzing a Sample in the Presence of Interferents," the entirety of which is hereby incorporated herein by reference.

In one embodiment, Eq. 13 and Eq. 14 can be used together to calculate a glucose concentration for either blood or a control solution. In another embodiment, the algorithm of Eq. 13 and Eq. 14 can be used for blood with a first set of calibration factors (i.e. a, p, and Z) and a second set of calibration factors can be used for the control solution. When using two different sets of calibration factors, the methods described herein for discriminating between a test fluid and a control solution can improve the effectiveness of the analyte concentration calculations.

Figure 8B:
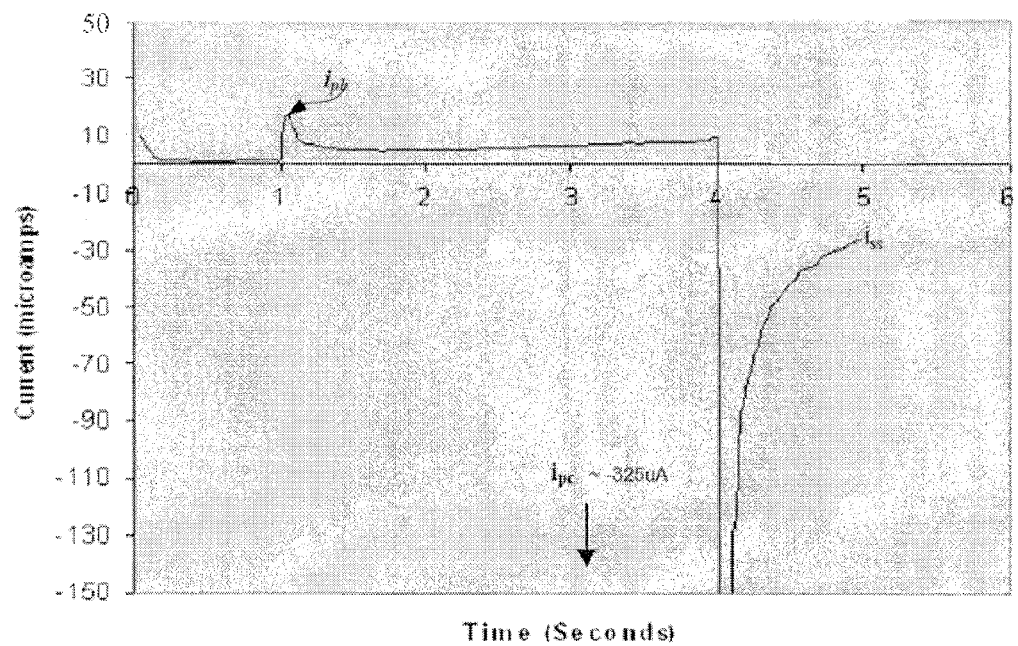
FIG. 8B illustrates a test current transient generated with the test voltages of FIG. 8A.

The example illustrated in FIGS. 7A and 7B shows the polarity of the first and second applied voltages as negative with a third applied voltage as positive when the electrode which is not coated with reagent acts as the reference electrode for the voltage measurement. However, the voltages applied can be of opposite polarity to the sequence illustrated in FIG. 7A if the electrode which is coated with reagent acts as the reference electrode for the voltage measurement. For example, in the preferred embodiment of FIGS. 8A and 8B, the polarity of the first and second applied voltages are positive with the polarity of the third applied voltage as negative. In both cases, the calculation of the glucose is the same because the electrode which is not coated with reagent acts as the anode during the first and second applied voltages, and the electrode which is coated with reagent acts as the anode during the third applied voltage.

In addition, if the test meter determines that the sample is control solution (as opposed to blood), the test meter can store the resulting glucose concentration of the control sample such that a user can review test sample concentration data separately from control solution data. For example, the glucose concentrations for control solutions can be stored in a separate database, can be flagged, and/or discarded (i.e., not stored or stored for a short period of time).

Another advantage of being able to recognize a control solution is that a test meter can be programmed to automatically compare the results (e.g., glucose concentration) of the test of the control solution with the expected glucose concentration of the control solution. For example, the test meter can be pre-programmed with the expected glucose level(s) for the control solution(s). Alternatively, a user could input the expected glucose concentration for the control solution. When the test meter recognizes a control solution, the test meter can compare the measured control solution glucose concentration with the expected glucose concentration to determine if the meter is functioning properly. If the measured glucose concentration is out of the expected range, the test meter can output a warning message to alert the user.

Fill Time Correction

In some embodiments, the analyte concentration can be corrected on the basis of the fill time of the sample. One example of such a method is disclosed in a co-pending patent application entitled "Systems, Devices and Methods for Improving Accuracy of Biosensors Using Fill Time," of Ronald C. Chatelier and Alastair M. Hodges, (application Ser. No. 12/649,594) filed on Dec. 30, 2009, and which is hereby incorporated by reference in its entirety. In such exemplary methods, a sample is introduced into an electrochemical cell of a sample analyzing device that has a working electrode and a counter electrode. An electric potential can be applied between the working and counter electrodes of the electrochemical cell and a fill time of the sample into, for example, a capillary space of the electrochemical cell, can be determined A prepulse time can be calculated in view of at least the fill time of the sample and an electric potential can be applied between the working electrode and the counter electrode for a length of time equal to the prepulse time. A concentration of the analyte in the sample can then be determined. By calculating the prepulse time in view of the fill time, more accurate results can be achieved for analyte concentration. For example, errors, such as those that can result from varying haematocrit levels across samples, can be accounted for, thereby leading to more accurate determinations of the concentrations of the analytes in the samples. In an alternative embodiment for detecting a concentration of an analyte in a sample, errors can be corrected for based on a determined initial fill velocity rather than a determined fill time. One example of such a method is disclosed in a co-pending patent application entitled "Systems, Devices and Methods for Measuring Whole Blood Haematocrit Based on Initial Fill Velocity," of Ronald C. Chatelier, Dennis Rylatt, Linda Raineri, and Alastair M. Hodges, (application Ser. No. 12/649,509) filed on Dec. 30, 2009, and which is hereby incorporated by reference in its entirety.

Temperature Correction

In some embodiments of the systems and methods of the present invention, a blood temperature correction can be applied to the test current values to provide an analyte concentration with an improved accuracy because of a reduced effect from temperature. A method for calculating a temperature corrected analyte concentration can include measuring a temperature value and calculating a temperature correction value $C_T$. The temperature correction value $C_T$ can be based on a temperature value and an analyte concentration, e.g., a glucose concentration. Accordingly, the temperature correction value $C_T$ can then be used to correct the analyte concentration for temperature.

Initially, an analyte concentration uncorrected for temperature can be obtained, such as the glucose concentration [G] from Equation 13, above. A temperature value can also be measured. The temperature can be measured using a thermistor or other temperature reading device that is incorporated into a test meter, or by way of any number of other mechanisms or means. Subsequently, a determination can be performed to determine whether the temperature value T is greater than a first temperature threshold $T_1$. For example, the temperature threshold $T_1$ can be about 15° C. If the temperature value T is greater than 15° C., then a first temperature function can be applied to determine the temperature correction value $C_T$. If the temperature value T is not greater than 15° C., then a second temperature function can be applied to determine the temperature correction value $C_T$.

The first temperature function for calculating the temperature correction value $C_T$ can be in the form of Equation 15:

$$C_T = -K_9(T-T_{RT}) + K_{10}[G](T-T_{RT}) \qquad \text{Eq. 15}$$

where $C_T$ is the correction value, $K_9$ is a ninth constant (e.g., 0.59), T is a temperature value, $T_{RT}$ is a room temperature value (e.g., 22° C.), $K_{10}$ is a tenth constant (e.g., 0.00004), and [G] is the glucose concentration. When T is about equal to $T_{RT}$, $C_T$ is about zero. In some instances, the first temperature function can be configured to have essentially no correction at room temperature such that variation can be reduced under routine ambient conditions. The second temperature function for calculating the second correction value $C_T$ can be in the form of Equation 16:

$$C_T = -K_{11}(T-T_{RT}) - K_{12}[G](T-T_{RT}) - K_{13}[G](T-T_1) + K_{14}[G](T-T_1) \qquad \text{Eq. 16}$$

where $C_T$ is the correction value, $K_{11}$ is an eleventh constant (e.g., 0.59), T is a temperature value, $T_{RT}$ is a room temperature value, $K_{12}$ is a twelfth constant (e.g., 0.00004), [G] is a glucose concentration, $K_{13}$ is a thirteenth constant (e.g., 1.2), $T_1$ is a first temperature threshold, and $K_{14}$ is a fourteenth constant (e.g., 0.005).

After $C_T$ is calculated using Equation 15, a couple of truncation functions can be performed to ensure that $C_T$ is constrained to a pre-determined range, thereby mitigating the risk of an outlier. In one embodiment $C_T$ can be limited to have a range of −10 to +10. For example, a determination can be performed to determine whether $C_T$ is greater than 10. If $C_T$ is greater than 10, then $C_T$ is set to 10. If $C_T$ is not greater than 10, then a determination is performed to determine whether $C_T$ is less than −10. $C_T$ can be set to −10 if $C_T$ is less than −10. If $C_T$ is a value already in between −10 and +10, then there generally is no need for truncation.

Once $C_T$ is determined, a temperature corrected glucose concentration can be calculated. For example, a determination can be performed to determine whether the glucose concentration uncorrected for temperature (e.g., [G]) is less than 100 mg/dL. If [G] is less than 100 mg/dL, then an Equation 17 can be used to calculate the temperature corrected glucose concentration $G_T$ by adding the correction value $C_T$ to the glucose concentration [G]:

$$G_T = [G] + C_T \qquad \text{Eq. 17}$$

If [G] is not less than 100 mg/dL, then an Equation 18 can be used to calculate the temperature corrected glucose concentration $G_T$ by dividing $C_T$ by one hundred, adding one; and then multiplying by the glucose concentration [G]:

$$G_T = [G]/[1 + 0.01 \times C_T] \qquad \text{Eq. 18}$$

Once a glucose concentration is determined that has been corrected for the effects of temperature, the glucose concentration can be output, e.g., to a display.

Age/Storage Correction

In some embodiments of the systems and methods of the present invention, a further correction factor can be applied to the calculated glucose concentration. This correction factor can be used to provide improved accuracy by correcting for the effect of age and/or storage conditions on sensor performance. For example, a parameter correlating to a physical property of the sensor can be measured and that parameter can be used to calculate a corrected analyte concentration. In some embodiments, the parameter correlating to a physical property of the sensor can be a measured capacitance of the sensor.

The measured capacitance of the sensor, e.g., an electrochemical cell of the type described in more detail above, can be related to the age and/or storage conditions of the sensor. By way of non-limiting example, the capacitance of an electrochemical cell can be affected by the slow flow of the adhesive used in the manufacture of the electrochemical cell from the spacer layer into the sample reaction chamber. As the sensor ages, such as during storage, particularly at elevated temperatures, the adhesive can flow into the reaction chamber and cover the reference and/or counter electrodes of the sensor. For example, the adhesive can cause a reduction in the area of the electrodes, which can affect the accuracy of measurements made by the sensor. The reduction in electrode area can also correlate with a reduction in the capacitance of the sensor. A measured capacitance of the sensor can therefore be used to calculate a correction factor that can be used to improve the accuracy of readings made using the sensor.

In one exemplary embodiment, a method for calculating a corrected analyte concentration can include measuring a physical property of the electrochemical cell, e.g., a capacitance, and calculating a correction factor $C_c$. The correction factor $C_c$ can be based on the measured physical property. Accordingly, the correction factor $C_c$ can be used to calculate a corrected analyte concentration.

Initially, an uncorrected analyte concentration can be obtained, such as the glucose concentration [G] from Equation 13, above. Alternatively, the analyte concentration used in the algorithms discussed below can be a corrected analyte concentration that has been previously corrected using any other correction methods, e.g., the temperature and/or fill time corrected analyte concentrations discussed in more detail above. A measured capacitance of the sensor can also be obtained, e.g., using the capacitance measurement methods discussed above. Subsequently, a determination can be performed to determine whether the measured capacitance value C is less than a capacitance threshold value $C_1$. In some embodiments, the capacitance threshold value $C_1$ can be an average or ideal capacitance of sensors of the same type. If the capacitance value C is less than the capacitance threshold value $C_1$ and if the uncorrected (or previously corrected) analyte concentration [G] is greater than an analyte concentration threshold $[G_1]$, then a capacitance correction function can be used to determine the correction factor $C_c$. If the capacitance value C is not less than a than the capacitance threshold value $C_1$ and/or if the uncorrected (or previously corrected) analyte concentration [G] is not greater than the analyte concentration threshold $[G_1]$, then the correction factor $C_c$ can be set to zero. For example, in one embodiment, the capacitance threshold value $C_1$ can be about 559 nanoFarad and the analyte concentration threshold $[G_1]$, e.g., a glucose concentration, can be about 100 mg/dL. Accordingly, if the capacitance value C and/or the analyte concentration [G] are with the predetermined range(s), the correction factor $C_c$ can be determined using a capacitance correction function, else the correction factor $C_c$ can be set to zero.

The capacitance correction function for calculating a capacitance correction factor $C_c$ when the measured capacitance value C is less than the capacitance threshold value $C_1$ and the uncorrected (or previously corrected) analyte concentration [G] is greater than an analyte concentration threshold $[G_1]$ can be in the form of Equation 19:

$$C_c = K_c(C_1 - C) \qquad \text{Eq. 19}$$

where $C_c$ is the correction factor, $K_c$ is an empirically derived constant (e.g., 0.152), $C_1$ is the capacitance threshold value (e.g., 559 nanoFarad), and C is the measured capacitance value.

After $C_c$ is calculated, e.g., using Equation 19, a couple of truncation functions can be performed to ensure that $C_c$ is constrained to a pre-determined range, thereby mitigating the risk of an outlier by limiting the maximum correction applied to the data. In one embodiment, if $C_c$ is greater than a cutoff value, $C_c$ can be set to the cutoff value. For example, a determination can be performed to determine whether $C_c$ is greater than a cutoff value, e.g, 5. If $C_c$ is greater than the cutoff value, e.g., 5, then $C_c$ is set to the cutoff value, e.g., 5. If $C_c$ is not greater than the cutoff value, then there generally is no need for truncation.

Once $C_c$ is determined, a capacitance corrected glucose concentration can be calculated. For example, a determination can be performed to determine whether the uncorrected (or previously corrected) analyte concentration [G] is less than an analyte concentration threshold $[G_1]$, e.g., 100 mg/dL if the analyte is glucose. If [G] is less than the analyte concentration threshold $[G_1]$, then no further correction is applied. If [G] is greater than the analyte concentration threshold $[G_1]$, then an Equation 20 can be used to calculate the capacitance corrected glucose concentration $G_c$ by dividing $C_c$ by one hundred, adding one, and then multiplying by the analyte concentration [G]:

$$G_c = [G]/[1 + 0.01 \times C_c]. \qquad \text{Eq. 18}$$

Once an analyte concentration is determined that has been corrected for the effects of age and/or storage, the glucose concentration can be output, e.g., to a display.

EXAMPLE 1

The development of an algorithm to correct for the age of sensors used in an electrochemical system is demonstrated by the following example. In the following example, the system included a sensor with two opposed electrodes, with reagents designed to react with the sample dried on one electrode. A plurality of samples was provided for analysis to test the performance of the systems, devices, and methods disclosed herein. The samples were blood samples that contained three different levels of haematocrit and two different levels of glucose, each of which were known so comparisons of the test results could be compared to the actual results to determine the accuracy of the systems, devices, and methods. The three levels of haematocrit were approximately 20%, 37-45%, and 60%. The two levels of glucose were approximately 250 mg/dL and 500 mg/dL. Testing three levels of haematocrit and two levels of glucose allowed the accuracy of the disclosed systems, devices, and methods to be confirmed over a broad spectrum of concentration levels.

Figure 9:
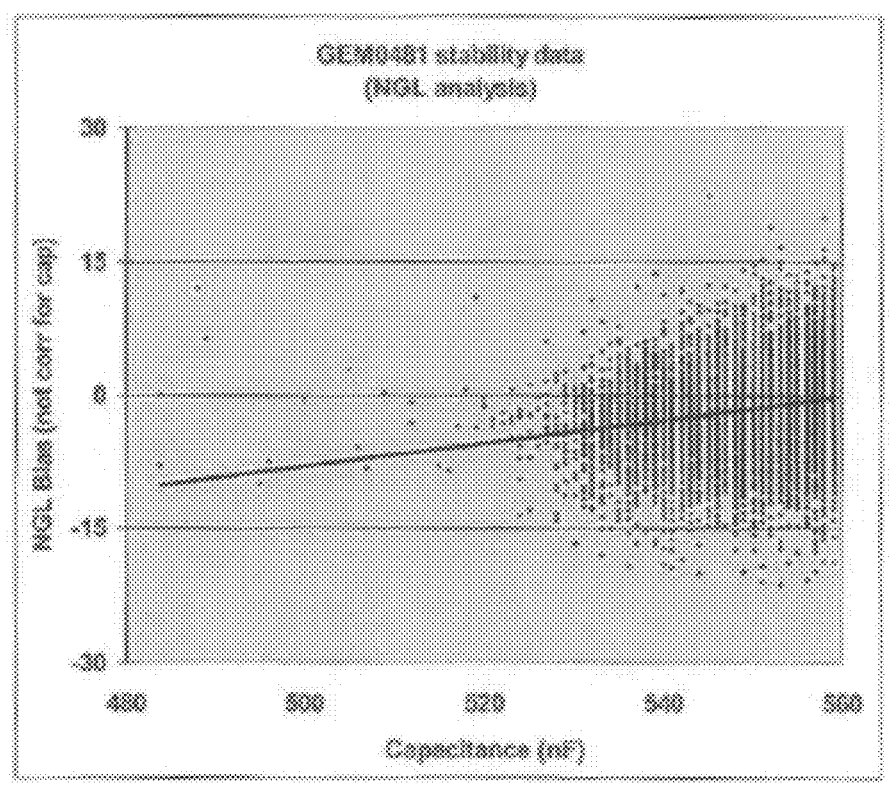
FIG. 9 is a chart showing a relationship between capacitance and bias percentage for a plurality of tests.

In this example, a first group of sensors was stored at 5° Celsius for 4-21 weeks. A second group of sensors was stored at 30° Celsius and 65% relative humidity for 4-21 weeks. The sensors were tested with the samples of blood discussed above. During the glucose measurements, a capacitance of the sensors was also calculated. Each sample was also tested using a YSI 2700 clinical instrument to give a baseline measurement of glucose against which the sensor-based measurements was compared to provide NGL bias data. FIG. 9, which shows NGL bias vs. capacitance, illustrates the data obtained in these tests. As illustrated in FIG. 9, the bias percentage correlates with capacitance. In particular, lower measured capacitance correlates with increased negative bias, as shown by the regression line in the chart.

EXAMPLE 2

The results of a capacitance correction algorithm are demonstrated by the following example. In this example, the data obtained from the experiment discussed in Example 1 was corrected based on the correction algorithm discussed in more detail above. Table 1 shows the improvement in glucose measurements obtained by applying the correction algorithm, the data represents the percentage of biases which are within a given number of mg/dL of the measurements made by the YSI 2700 clinical instrument when G<80 mg/dL or within a give % of the measurements made by the YSI 2700 clinical instrument when G≥80 mg/dL. Also shown in Table 1 are the mean bias and the root-mean-square bias.

TABLE 1

|  | Uncorrected data | Corrected data |
| --- | --- | --- |
| % biases within 10% or 10 mg/dL | 93.48 | 94.84 |
| % biases within 12% or 12 mg/dL | 97.29 | 97.73 |
| % biases within 15% or 15 mg/dL | 99.21 | 99.29 |
| Mean bias | −1.67 | −0.25 |
| RMS bias | 5.45 | 5.15 |

The capacitance corrected data in the right column of the table shows the improvement in each parameter when the glucose values were corrected using the measured capacitance.

EXAMPLE 3

The results of testing the use of the capacitance correction algorithm with more severely aged sensors are demonstrated by the following example. In this example, the algorithm was challenged with a much larger data set of 60,864 sensors, where the sensors were stored at 5-40° Celsius. The results in Table 2 show a consistent improvement in the accuracy and precision when using the disclosed capacitance correction algorithm.

TABLE 2

|  | Uncorrected data | Corrected data |
| --- | --- | --- |
| % biases within 10% or 10 mg/dL | 91.09 | 93.14 |
| % biases within 12% or 12 mg/dL | 95.54 | 96.77 |
| % biases within 15% or 15 mg/dL | 98.47 | 98.94 |
| Mean bias | −0.26 | 0.41 |
| Global SD bias | 5.83 | 5.40 |
| RMS bias | 5.83 | 5.42 |
| Pooled precision | 2.15 | 2.18 |
| Number of tests | 60,864 | 60,864 |

EXAMPLE 4

The results of the use of the capacitance correction algorithm with un-aged (freshly manufactured) sensors at high temperatures are demonstrated by the following example. In this example, freshly manufactured sensors were tested over a temperature range of 5-45° Celsius. The results in Table 3 show that the performance of the sensors is not significantly degraded when the capacitance correction algorithm is applied over a variety of simulated high-temperature weather conditions.

TABLE 3

|  | Uncorrected data | Corrected data |
| --- | --- | --- |
| % biases within 10% or 10 mg/dL | 96.39 | 96.37 |
| % biases within 12% or 12 mg/dL | 98.73 | 98.71 |
| % biases within 15% or 15 mg/dL | 99.73 | 99.71 |
| Mean bias | −0.51 | −0.49 |
| Global SD bias | 4.68 | 4.68 |
| RMS bias | 4.71 | 4.70 |
| Pooled precision | 2.44 | 2.43 |
| Number of tests | 5,178 | 5,178 |

EXAMPLE 5

The results of the use of the capacitance correction algorithm with multiple sensor manufacturing lots and blood samples over an extended haematocrit and glucose range at room temperature are demonstrated by the following example. In this example, sensors were tested at room temperature. The results in Table 4 show that the capacitance correction algorithm also provides accurate results over an extended haematocrit and glucose range at room temperature.

TABLE 4

|  | Uncorrected data | Corrected data |
| --- | --- | --- |
| % biases within 10% or 10 mg/dL | 98.46 | 98.43 |
| % biases within 12% or 12 mg/dL | 99.39 | 99.38 |
| % biases within 15% or 15 mg/dL | 99.83 | 99.83 |
| Mean bias | −0.02 | 0.12 |
| Global SD bias | 3.81 | 3.84 |
| RMS bias | 3.81 | 3.84 |
| Pooled precision | 1.86 | 1.88 |
| Number of tests | 50,997 | 50,997 |

While the invention has been described in terms of particular variations and illustrative figures, one skilled in the art will recognize that the invention is not limited to the variations or figures described. In addition, where methods and steps described above indicate certain events occurring in certain order, those skilled in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. All publications and references cited herein are expressly incorporated herein by reference in their entirety.

What is claimed is:

1. A method for determining a concentration of an analyte in a sample, the method comprising:
   introducing a sample including an analyte into an electrochemical cell of a sample analyzing device to cause a transformation of the analyte, the electrochemical cell having a first electrode and a second electrode;

determining a measurement of a parameter correlating to a physical property of the electrochemical cell, said parameter comprising a measured capacitance of the electrochemical cell;

calculating a correction factor, wherein said correction factor is in view of at least said parameter; and determining a first analyte concentration and a corrected concentration of the analyte in view of the correction factor, wherein determining said measured capacitance of the electrochemical cell further comprises:

applying a first test voltage between the first electrode and the second electrode after the presence of sample has been detected in the test strip for a first time interval to determine whether sample or a control solution has been introduced into the test strip;

applying a second test voltage between the first electrode and the second electrode for a second time interval sufficient to oxidize a reduced mediator at the second electrode, the second test voltage having a higher absolute magnitude than that of the first test voltage, the second test voltage having an AC voltage component and a DC voltage component, the AC voltage component being applied at a predetermined amount of time after the application of the second test voltage, the DC voltage component having a magnitude to cause a limiting test current at the second electrode, the second electrode not having a reagent layer coating;

applying a third test voltage between the first electrode and the second electrode for a third time interval following the application of the second test voltage sufficient to oxidize a reduced mediator at the first electrode; and processing a portion of the test currents, resulting from the AC voltage component, into a capacitance value, and in which the first analyte concentration is calculated based on test current values during the second time interval and the third time interval and the corrected analyte concentration is calculated based on the first analyte concentration and the correction factor.

2. The method of claim 1, wherein said physical property is related to at least one of an age of electrochemical cell and a storage condition of the electrochemical cell.

3. The method of claim 2, wherein said storage condition comprises a storage temperature and a storage time.

4. The method of claim 1, wherein the sample analyzing device comprises a glucose sensor.

5. The method of claim 1, wherein the sample analyzing device comprises an immunosensor.

6. The method of claim 1, wherein the sample comprises blood.

7. The method of claim 6, wherein the blood comprises whole blood.

8. The method of claim 1, wherein the predetermined amount of time for applying the AC voltage component is equal to 0.3 to 0.4 seconds from application of the DC voltage component of the first test voltage.

9. The method of claim 1, wherein the predetermined amount of time for applying the AC voltage component is a time where a test current transient as a function of time is equal to zero.

10. The method of claim 1, wherein the predetermined amount of time is a time required for a peak current value to decay by about 50 percent.

11. A method for measuring a corrected analyte concentration, the method comprising:

applying a sample containing an analyte to a test strip;

applying to the sample a first test voltage for a first time interval between a first electrode and a second electrode after the presence of sample has been detected in the test strip to determine whether sample or a control solution has been introduced into the test strip;

applying to the sample a second test voltage for a second time interval between the first electrode and the second electrode sufficient to oxidize a reduced mediator at the second electrode and having a higher absolute magnitude than that of the first test voltage;

following the application of the second test voltage, applying to the sample a third test voltage for a third time interval between the first electrode and the second electrode sufficient to oxidize the reduced mediator at the first electrode;

calculating a first analyte concentration in the sample based on test current values during the second time interval and the third time interval;

determining a capacitance of the test strip; and calculating a capacitance corrected analyte concentration based on the first analyte concentration and the capacitance wherein said determining a capacitance of the test strip further comprises:

applying the second test voltage between the first electrode and the second electrode, the second test voltage having an AC voltage component and a DC voltage component, the AC voltage component being applied at a predetermined amount of time after the application of the second test voltage, the DC voltage component having a magnitude sufficient to cause a limiting test current at the second electrode, the second electrode not having a reagent layer coating; and processing a portion of the test currents, resulting from the AC voltage component, into a capacitance value.

12. The method of claim 11, wherein the step of calculating the capacitance corrected analyte concentration comprises:

calculating a correction factor based on the capacitance and the first analyte concentration, wherein the capacitance corrected analyte concentration is calculated based on the first analyte concentration and the correction factor.

13. The method of claim 12, wherein the step of calculating the capacitance corrected analyte concentration further comprises:

dividing the correction factor by one hundred and adding one to give an intermediate term; and multiplying the intermediate term by the first analyte concentration to give a capacitance corrected analyte concentration.

14. The method of claim 12, further comprising:

determining if the correction factor is greater than a correction factor threshold value, then setting the correction factor to the correction factor threshold value.

15. The method of claim 12, wherein the correction factor is about zero when the capacitance is about equal to a predetermined ideal capacitance of the test strip.

16. The method of claim 11, wherein the capacitance corrected analyte concentration is calculated when the capacitance is less than a first capacitance threshold and the first analyte concentration is greater than a first analyte concentration threshold.

17. The method of claim 11, wherein the analyte comprises glucose.

18. The method of claim 11, wherein the predetermined amount of time for applying the AC voltage component is equal to 0.3 to 0.4 seconds from application of the DC voltage component of the second test voltage.

19. The method of claim 11, wherein the predetermined amount of time for applying the AC voltage component is a time where a test current transient as a function of time is equal to zero.

20. The method of claim 11, wherein the predetermined amount of time is a time required for a peak current value to decay by about 50 percent.

* * * * *